(12) United States Patent
Shetty et al.

(10) Patent No.: US 11,161,875 B2
(45) Date of Patent: Nov. 2, 2021

(54) INHIBITION OF PULMONARY FIBROSIS WITH NUTLIN-3A AND PEPTIDES

(71) Applicant: BOARD OF REGENTS, THE UNIVERSITY OF TEXAS SYSTEM, Austin, TX (US)

(72) Inventors: Sreerama Shetty, Tyler, TX (US); Steven Idell, Tyler, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/702,101

(22) Filed: Dec. 3, 2019

(65) Prior Publication Data

US 2020/0165298 A1    May 28, 2020

Related U.S. Application Data

(63) Continuation of application No. 15/727,828, filed on Oct. 9, 2017, now abandoned, which is a continuation of application No. 15/455,670, filed on Mar. 10, 2017, now Pat. No. 10,377,796, which is a continuation of application No. 14/775,895, filed as application No. PCT/US2014/030147 on Mar. 17, 2014, now Pat. No. 9,630,990.

(60) Provisional application No. 61/800,117, filed on Mar. 15, 2013.

(51) Int. Cl.
| | |
|---|---|
| A61K 38/08 | (2019.01) |
| A61K 47/64 | (2017.01) |
| C07K 7/06 | (2006.01) |
| C07K 19/00 | (2006.01) |
| C07K 7/08 | (2006.01) |
| A61K 38/17 | (2006.01) |
| A61K 31/497 | (2006.01) |
| A61K 9/00 | (2006.01) |
| A61K 38/00 | (2006.01) |

(52) U.S. Cl.
CPC ........... *C07K 7/06* (2013.01); *A61K 9/007* (2013.01); *A61K 9/0019* (2013.01); *A61K 31/497* (2013.01); *A61K 38/08* (2013.01); *A61K 38/177* (2013.01); *A61K 47/64* (2017.08); *A61K 47/645* (2017.08); *C07K 7/08* (2013.01); *A61K 38/00* (2013.01); *C07K 2319/10* (2013.01)

(58) Field of Classification Search
CPC ........ A61K 38/08; A61K 38/10; A61K 47/64; A61K 47/645; C07K 7/06; C07K 7/08; C07K 2319/01–10
See application file for complete search history.

(56) References Cited

U.S. PATENT DOCUMENTS

| | | | |
|---|---|---|---|
| 4,021,387 A | 5/1977 | Goetzl et al. | |
| 4,628,045 A | 12/1986 | Hahn | |
| 4,719,288 A | 1/1988 | Fuhrer et al. | |
| 4,816,449 A | 3/1989 | Hahn | |
| 5,358,934 A | 10/1994 | Borovsky et al. | |
| 5,559,209 A | 9/1996 | Nishimoto | |
| 5,728,680 A | 3/1998 | Morozov et al. | |
| 6,126,939 A | 10/2000 | Eisenbach-Schwartz et al. | |
| 7,494,976 B2 | 2/2009 | Sessa | |
| 8,058,227 B2 | 11/2011 | Hoffman et al. | |
| 8,349,798 B2 | 1/2013 | Sessa | |
| 8,487,072 B2 | 7/2013 | Beliveau et al. | |
| 8,697,840 B2 | 4/2014 | Shetty et al. | |
| 9,630,990 B2 | 4/2017 | Shetty et al. | |
| 9,908,915 B2 | 3/2018 | Sessa et al. | |
| 10,377,796 B2 | 8/2019 | Shetty et al. | |
| 2002/0077283 A1 | 6/2002 | Sessa | |
| 2003/0113271 A1 | 6/2003 | Katyama et al. | |
| 2003/0165510 A1 | 9/2003 | Sessa | |
| 2007/0140976 A1 | 6/2007 | Chen et al. | |
| 2007/0154404 A1 | 7/2007 | Colombo et al. | |
| 2009/0075875 A1 | 3/2009 | Hoffman et al. | |

(Continued)

FOREIGN PATENT DOCUMENTS

| | | |
|---|---|---|
| WO | WO 2001/011038 | 2/2001 |
| WO | WO 2002/020768 | 3/2002 |

(Continued)

OTHER PUBLICATIONS

"Retsch technology sales literature for light scatterers", downloaded from https://www.retsch-technology.com/products/laser-light-scattering/, on Jun. 11, 2019.

(Continued)

*Primary Examiner* — Jeffrey E. Russel
(74) *Attorney, Agent, or Firm* — Parker Highlander PLLC

(57) ABSTRACT

In fibrotic lung fibroblasts, basal levels of p53 protein (and miR-34a) are markedly suppressed, leading to reduced p53-mediated inhibition of uPA and uPAR, or concurrent induction of PAI-1. These changes contribute to excessive FL-fibroblast proliferation and production of extracellular matrix (ECM), and, therefore, pulmonary fibrosis. These processes are reversed by treating the cells, and treating subjects suffering from idiopathic pulmonary fibrosis (IPF) with the small organic molecule nutlin-3a (NTL) or with a peptide, CSP-4 (SEQ ID NO:1), or variants or derivatives or multimers of this peptide, which increase p53 levels by inhibiting MDM2-mediated degradation of p53 protein. Use of these compounds serves as a new approach to the treatment of IPF, as they restore p53 expression and p53-mediated changes in the uPA-fibrinolytic system in FL-fibroblasts and restrict production and deposition of ECM.

16 Claims, 13 Drawing Sheets
Specification includes a Sequence Listing.

(56) References Cited

U.S. PATENT DOCUMENTS

| | | |
|---|---|---|
| 2009/0227515 A1 | 9/2009 | Shetty et al. |
| 2011/0218152 A1 | 9/2011 | Beliveau |
| 2013/0224163 A1 | 8/2013 | Head et al. |
| 2015/0141340 A1 | 5/2015 | Sessa |
| 2016/0022577 A1 | 1/2016 | Flynn et al. |
| 2016/0272678 A1 | 9/2016 | Shetty et al. |
| 2016/0279209 A1 | 9/2016 | Williams et al. |
| 2017/0128520 A1 | 5/2017 | Eveleth et al. |
| 2017/0253632 A1 | 9/2017 | Shetty et al. |
| 2018/0086791 A1 | 3/2018 | Shetty et al. |

FOREIGN PATENT DOCUMENTS

| | | |
|---|---|---|
| WO | WO 2003/016540 | 2/2003 |
| WO | WO 2008/046228 | 4/2008 |
| WO | WO 2009/074634 | 6/2009 |
| WO | WO 2009/111625 | 9/2009 |
| WO | WO 2010/030813 | 3/2010 |
| WO | WO 2011/098552 | 8/2011 |
| WO | WO 2013/184482 | 12/2013 |
| WO | WO 2014/145389 | 9/2014 |
| WO | WO 2015/066664 | 5/2015 |
| WO | WO 2015/080943 | 6/2015 |
| WO | WO 2015/080980 | 6/2015 |
| WO | WO 2020/055812 | 3/2020 |
| WO | WO 2020/055824 | 3/2020 |

OTHER PUBLICATIONS

Altman et al., "Predictors of survival in systemic sclerosis (scleroderma)", *Arthritis Rheum.*, 34:403-413, 1991.

Anderson, "The caveolae membrane system", *Annu Rev Biochem*, 67:199-225, 1998.

Arbuzova et al., "Membrane Binding of Peptides Containing Both Basic and Aromatic Residues—Experimental Studies with Peptides Corresponding to the Scaffolding Region of Caveolin and the Effector Region of MARCKS", *Biochemistry*, 39(33): 10330-9, 2000.

Bellini et al., "The role of the fibrocytes, a bone marrow-derived mesenchymal progenitor, in reactive and reparative fibrosis", *Lab Invest*, 2007.

Beon et al., "Myofibroblast induction and microvascular alteration in scleroderma lung fibrosis", *Clin Exp Rheumatol*, 22: 733-742, 2004.

Bernatchez et al., "Dissecting the molecular control of endothelial NO synthase by caveolin-1 using cell-permeable peptides", *Proc Natl Acad Sci USA*, 102:761-766, 2005.

Bhandary et al., "Regulation of alveolar epithelial cell apoptosis and pulmonary fibrosis by coordinate expression of components of the fibrinolytic system", *Am J Physiol Lung Cell Mol Physiol.*, 302: L463-L473, 2012.

Bogatkevich et al., "Contractile Activity and Smooth Muscle alpha-actin organization in thrombin-induced human lung myofibroblasts", *J. Physiol Lung CEll Mol Physiol*, 85:L334-L343, 2003.

Bogatkevich et al., "Thrombin differentiates normal lung fibroblasts to a myofibroblast phenotype via the proteolytically activated receptor-1 and a protein kinase C-dependent pathway", *J Biol Chem.*, 276:45184-45192, 2001.

Bowie et al., "Deciphering the message in protein sequences: tolerance to amino acid substitutions", Science, 247: 1306-1310, 1990.

Bucci et al., "In vivo delivery of the caveolin-1 scaffolding domain inhibits nitric oxide synthesys and reduces inflammation", *Nature Med*, 6:1362-1367, 2000.

Bussone et al., "Interstitial lung disease in systemic sclerosis", *Autoimmunity Reviews*, 10:248-255, 2011.

CAS RN 246246-98-9, STN Entry Date Dec. 31, 1998.

Cohen et al., "Caveolin-1 null mice develop cardiac hypertrophy with hyperactivation of p42/44 MAP kinase in cardiac fibroblasts", *Am J Physiol Cell Physiol.*, 284:C457-474, 2003.

Couet et al., "Identification of peptide and protein ligands for the caveolin-scaffolding domain—Implications for the interaction of caveolin with caveolae-associated proteins", *J. Biol Chem.*, 272:6525-6533, 1997.

Couet et al., "Interaction of a receptor tyrosine kinase, EGF-R, with caveolins—Caveolin binding negatively regulates tyrosine and serine/threonine kinase activities", *J Bioi Chem.*, 272:30429-30438, 1997.

Cui et al., "Identification of specific domain responsible for JNK2alpha2 autophosphorylation", *J. Bioi. Chem.*, 280:9913-9920, 2005.

De la Torre et al., "On choosing the right ether for peptide precipitation after acid cleavage", *Journal of Peptide Science*, 14(3), 360-363, 2008.

Drab et al., "Loss of caveolae, vascular dysfunction, and pulmonary defects in caveolin-1 gene-disrupted mice", Science, 293:2449-2452, 2001.

Epand et al., "Caveolin Scaffolding Region and Cholesterol-rich Domains in Membranes", *Journal of Molecular Biology*, 345(2): 339-350, 2005.

Extended European Search Report issued in European Patent Application No. 14 76 2435, dated Nov. 17, 2016.

Finch et al., "Bleomycin-induced scleroderma", *J Rheumatol*,7:651-659, 1980.

Galbiati et al., "Expression of caveolin-1 and -2 in differentiating PC12 cells and dorsal root ganglion neurons: caveolin-2 is up-regulated in response to cell injury", *Proc Natl Acad Sci USA*, 95:10257-10262, 1998.

Gardenhire et al., "A guide to aerosol delivery devices for respiratory therapists." *American Association for Respiratory Care* (2013): 1-56.

Gray et al., "Partially degraded fibrin(ogen) stimulates fibroblast proliferation in vitro", *Am J Respirator Cell Mol Biol.*, 12: 684-690, 1995.

Gunther et al., "Prevention of bleomycin-induced lung fibrosis by aerosolization of heparin or urokinase in rabbits." *American journal of respiratory and critical care medicine* 168.11 (2003): 1358-1365.

Guo et al., "Involvement of caveolin-1 in the Jak-Stat signaling pathway and infectious spleen and kidney necrosis virus infection in mandarin fish (*Siniperca chua tsi*)", *Molecular Immunology*, 48(8): 992-1000, 2011.

Hartmann et al., "TIP peptide inhalation in experimental acute lung injury: effect of repetitive dosage and different synthetic variants." *BMC anesthesiology* 14.1 (2014): 42.

Hiemenz, "Principles of colloid and surface chemistry, $2^{nd}$ edition" (1986) ISBN 0-8247-7476-0.

Hong et al., "Differentiation of human circulating fibrocytes as mediated by transforming growth factor-beta and peroxisome proliferators activated receptor-gamma", *J Bioi Chem*, 2007.

Horton et al., "Phase behavior and the partitioning of caveolin-1 scaffolding domain peptides in model lipid bilayers", *Journal of Colloid and Interface Science*, 304(1): 67-76, 2006.

Hua et al., "Endothelin-1 activates mesangial cell ERK1/2 via EGF-receptor transactivation and caveolin-1 interaction", *Am J Physiol Renal Physiol*, 284:F303-312, 2003.

Huang, et al., "Reduced transcriptional activity in the p53 pathway of senescent cells revealed by the MDM2 antagonist nutlin-3", *Aging*,2009, 1(10), 845-54.

International Preliminary Report on Patentability issued in International Application No. PCT/US2014/030147, dated Sep. 24, 2015.

International Search Report and Written Opinion issued in International Application No. PCT/US2014/030147, dated Aug. 6, 2014.

Kasper et al., "Loss of caveolin-1 expression in type I pneumocytes as an indicator of subcellular alterations during lung fibrogenesis", *Histochem Cell Biol*, 109:41-48, 1998.

Kim et al., "Alveolar epithelial cell mesenchymal transition develops in vivo during pulmonary fibrosis and is regulated by the extracellular matrix", Proc Natl Acad Sci USA, 1 03: 13180-13185, 2006.

Le Saux et al., "Down-regulation of caveolin-1, an inhibitor of transforming growth factor-β signaling, an acute allergen-induced airway remodeling", *The Journal of Biological Chemistry*, 283(9): 5760-5768, 2008.

Levin et al., "Double barrel shotgun scanning of the caveolin-1 scaffolding domain", *ACS Chemical Biology*, 2(7): 493-500, 2007.

(56) References Cited

OTHER PUBLICATIONS

Lisanti et al., "Characterization of caveolin-rich membrane domains isolated from an endothelial-rich source: implications for human disease", *J Biol Chem*, 126: 111-126, 1994.
Mimura et al., "Constitutive phosphorylation of focal adhesion kinase is involved in the myofibroblast differentiation of scleroderma fibroblasts", *J Invest Dermatol*, 124: 886-892, 2005.
Moore et al., "CCR2-mediated recruitment of fibrocytes to the alveolar space after fibrotic injury", *Am J Pathol*, 166: 675-684, 2005.
Muller et al., "Redistribution of glycolipid raft domain components induces insulin-mimetic signaling in rat adipocytes", *Mol Cell Biol.*, 21:4553-4567, 2001.
Odajima et al., "Loss of caveolin-1 in bronchiolization in lung fibrosis", *Journal of Histochemistry & Cytochemistry*, 55(9): 899-909, 2007.
Oka et al., "Caveolin interaction with protein kinase C", *J Biol Chem*, 272:33416-33421, 1997.
Okamoto et al., "Caveolins, a family of scaffolding proteins for organizing 'pre-assembled signaling complexes' at the plasma membrane", *J Biol Chem*, 273:5419-5422, 1998.
Osier et al., "Intratracheal Inhalation vs Intratracheal Instillation: Differences in Particle Effects," *Fundam. Appl. Toxicol.*, 40:220-227, 1997.
Palmer, Brian; "The science of sea spray", dated May 21, 2015, downloaded from https://www.nrdc.org/onearth/science-sea-spray, on Oct. 25, 2018.
Pannu et al., "Transforming Growth Factor-beta receptor type I-dependent fibrogenic gene programls mediated via activation of Smad1 and ERK1/2 pathways", *J Biol Chem*, 282:10405-10413, 2007.
Phillips et al., "Circulating fibrocytes traffic to the lungs in response to CXCL 12 and mediate fibrosis", *J Clin Invest*, 114: 438-446, 2004.
Quan et al., "The role of the circulating fibrocytes in fibrosis", *Curr Rheumatol Rep*, 8: 145-150, 2006.
Razani et al., "Caveolae: from cell biology to animal physiology", *Pharmacal Rev*, 54:431-467, 2002.
Razani et al., "Caveolin-1 null mice are viable but show evidence of hyperproliferative and vascular abnormalities", *J Biol Chem.*, 276:38121-38138, 2001.
Razani et al., "Regulation of cAMP-mediated signal transduction via interaction of caveolins with the catalytic subunit of protein kinase A", *J Biol Chem.*, 274:26353-26360, 1999.
Respaud et al., "Effect of formulation on the stability and aerosol performance of a nebulized antibody." *MAbs*. vol. 6. No. 5. Taylor & Francis, 2014.
Rybin et al., "Activated protein kinase C isoforms target to cardiomyocyte caveolae: stimulation of local protein phosphorylation", *Circ Res*, 84: 980-988, 1999.
Scherer et al., "Caveolin isoforms differ in their N-terminal protein sequence and subcellular distribution. Identification and epitope mapping of an isoform-specific monoclonal antibody probe", *J Biol Chem.*, 270:16395-16401, 1995.
Sedding et al., "Caveolin-1 facilitates mechanosensitive protein kinase B (Akt) signaling in vitro and in vivo", *Circ Res*, 96: 635-642, 2005.
Sharma et al., "Bleomycin-induced scleroderma", *JAPI*52:76-77, 2004.
Shaul et al., "Role of plasmalemmal caveolae in signal transduction", *AJP Lung Cell Mol Phys*, 275:L843-L851, 1998.
Shetty et al., "Regulation of Airway and Alveolar Epithelial Cell Apoptosis by p53-Induced Plasminogen Activator Inhibitor-1 during Cigarette Smoke Exposure Injury", *American Journal of Respiratory Cell and Molecular Biology*, 47(4), 474-83, 2012.
Shi-wen et al., "Constitutive ALK5-independent c-Jun N-Terminal Kinase activation contributes to endothelin-1 overexpression in pulmonary fibrosis: evidence of an autocrine endothelin loop operating through the endothelin A and B receptors", *Mol Cel Biol*, 26; 5518-5527, 2006.
Shi-wen et al., "Endothelin-1 promotes myofibroblast induction through the ETA receptor via a rae/ P13 kinase/Akt-dependent pathway and is essential for the enhanced contractile phenotype of fibrotic fibroblasts", *MBC*, 15: 2707-2719, 2004.
Silver, "Interstitial lung disease of systemic sclerosis", *Int Rev Immunol.*, 12:281-291, 1995.
Song et al., "Co-precipitation and direct interaction of Ras with caveolin, an integral membrane protein of caveolae microdomains", *J Biol Chem*, 271 :9690-9697, 1996.
Sowa et al., "Distinction between signaling mechanisms in lipid rafts vs. caveolae", *Proc Natl Acad Sci USA*, 98: 14072-14077, 2001.
Steen et al., "Changes in causes of death in systemic sclerosis", *Ann Rheum Dis*, 66: 940-944, 2007.
Tashkin et al., "Cyclophosphamide versus placebo in scleroderma lung disease", *N Engl J Med*, 354: 2655-2666, 2006.
Thannickal et al., "Myofibroblast differentiation by transforming growth factor-beta 1 is dependent on cell adhesion and integrin signaling via focal adhesion kinase", *J Biol Chem*, 278: 12384-12389, 2003.
Toker et al., "Akt/Protein Kinase B regulated by autophosphorylation in the hypothetical PDK-2 site", *J Biol Chem*, 275: 8271-8274, 2000.
Tourkina et al., "Anti-fibrotic and anti-inflammatory roles of caveolin-1 in scleroderma", ASCB Meeting, San-Diego, Dec. 2006, Abstract L66.
Tourkina et al., "Antifibrotic properties of caveolin-1 scaffolding domain in vitro and in vivo", *AM J Physiol Lung Cell Mol Physiol.*, 294: L843-L861, 2008.
Tourkina et al., "Caveolin-1 regulates collagen expression through MEKIERK signaling and differentiation normal lung fibroblasts in myofibroblasts", ASCB Meeting, Washington, DC, Dec. 2005, Abstract 370.
Tourkina et al., "Curcumin-induced apoptosis in scleroderma lung fibroblasts: Role of protein kinase Ce", *American Journal of Respiratory Cellular and Molecular Biology*, 31:28-35, 2004.
Tourkina et al., "Depletion of PKC-epsilon in normal and scleroderma lung fibroblasts has opposite effects on tenascin expression", *Arthritis and Rheum*, 44:1370-1381, 2001.
Tourkina et al., "Opposing effects of protein kinase C alpha and protein kinase C epsilon on collagen expression by human lung fibroblasts are mediated via MEKIERK and caveolin-1 signaling", *J Biol Chem*, 280:13879-13887, 2005.
Uhal et al., "Alveolar epithelial cell death adjacent to underlying myofibroblasts in advanced fibrotic human lung", *Am J Physiol Lung Cell Mol Physiol*, 275:L 1192-L 1199, 1998.
Van de Water et al., "Animal models of scleroderma: contrasts and comparisons", *Intern Rev Immunol*, 12:201-216, 1995.
Vassilev et al., "In Vivo Activation of the p53 Pathway by Small-Molecule Antagonists of MDM2", *Science*, 2004, 303, 844-8.
Vyalov et al., "Rat alveolar myofibroblasts acquire alpha-smooth muscle actin expression during bleomycin-induced pulmonary fibrosis", *Am J Pathol*, 143: 1754-1765, 1993.
Wanaski et al., "Caveolin Scaffolding Region and the Membrane Binding Region of Src Form Lateral Membrane Domains", *Biochemistry*, 42( 1): 42-56, 2003.
Wang et al., "Caveolin-1: a critical regulator of lung fibrosis in idiopathic pulmonary fibrosis", *J Exp Med*, 203; 2895-2906, 2006.
Wells, "Additivity of mutational effects in proteins", *Biochemistry*, 29: 8509-8517, 1990.
Wender et al., "The design, synthesis, and evaluation of molecules that enable or enhance cellular uptake: peptoid molecular transporters", *Proc Natl Acad Sci USA*, 97:13003-13008, 2000.
White et al., "Negative regulation of myofibroblast differentiation by PTEN (Phosphatase and Tensin Homolog deleted on chromosome 10)", *Am J Respir Crit Care Med.*, 173: 112-121, 2006.
Wu et al., "Detection of epithelial to mesenchymal transition in airways of a bleomycin induced pulmonary fibrosis model derived from an alpha-smooth muscle actin-Cre transgenic mouse", *Respir Res.*, 8:1, 2007.
Yamamoto et al., "Animal model of sclerotic skin 1: local injections of bleomycin induce sclerotic skin mimicking scleroderma", *J Invest Dermatol.*, 112:456-462, 1999.

(56) References Cited

OTHER PUBLICATIONS

Zhang et al., "Lung fibroblast alpha-smooth muscle actin expression and contractile phenotype in bleomycin-induced pulmonary fibrosis", *Am J Pathol*, 148:527-537, 1996.

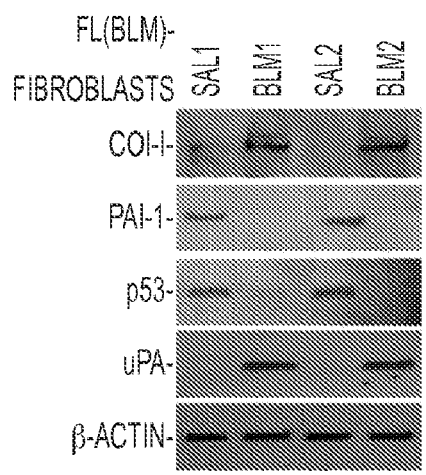
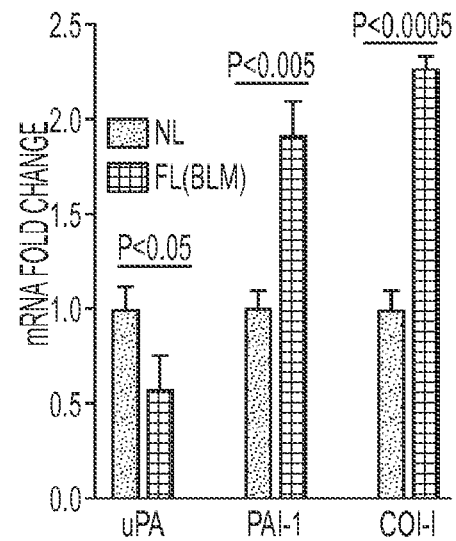
FIG. 5A
FIG. 5B
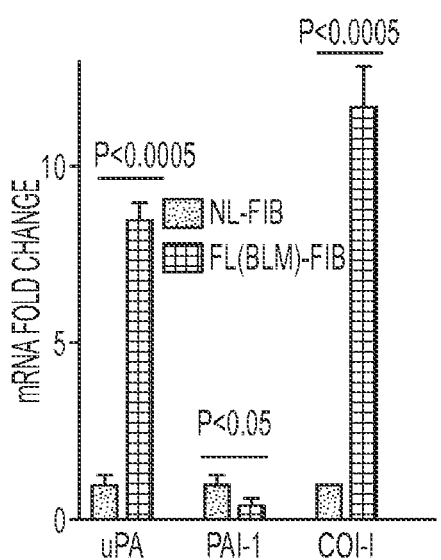
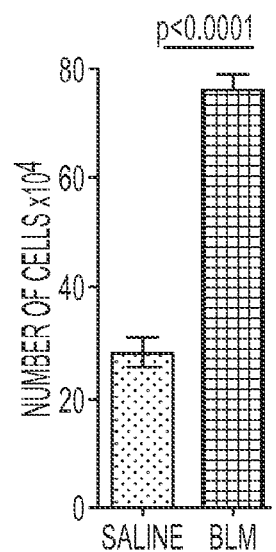
FIG. 5C
FIG. 5D

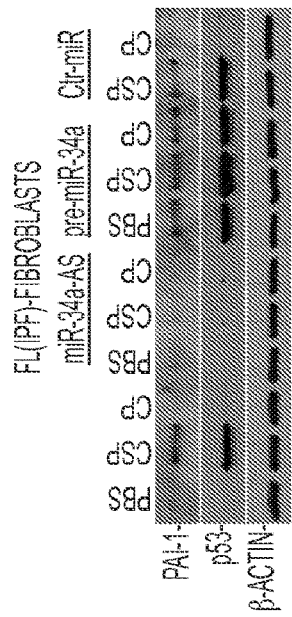
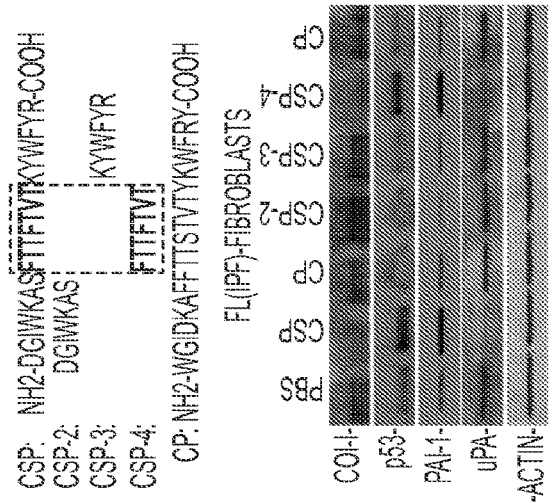
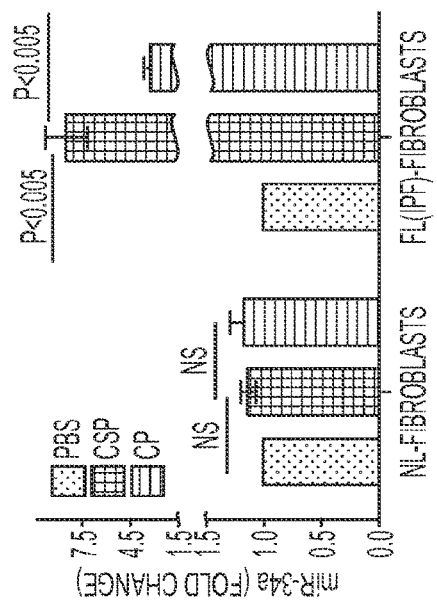
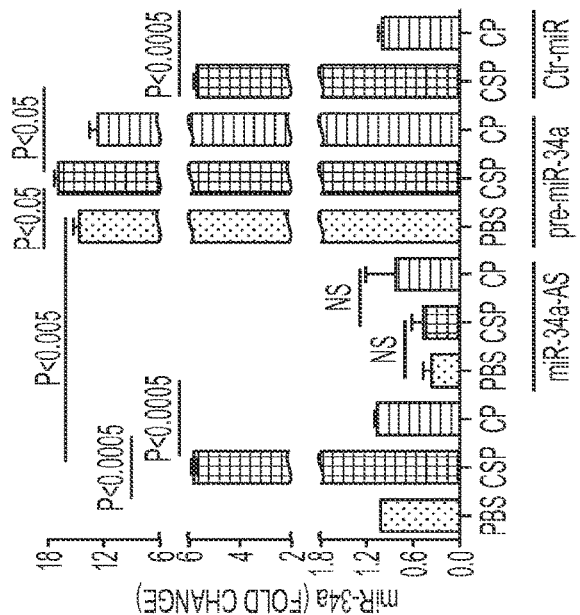
FIG. 6A
FIG. 6B
FIG. 6C
FIG. 6D

INHIBITION OF PULMONARY FIBROSIS WITH NUTLIN-3A AND PEPTIDES

This application is a continuation of U.S. patent application Ser. No. 15/727,828, filed Oct. 9, 2017, which is a continuation of U.S. patent application Ser. No. 15/455,670, filed Mar. 10, 2017, now U.S. Pat. No. 10,377,796, which is continuation of U.S. patent application Ser. No. 14/775,895, filed Sep. 14, 2015, now U.S. Pat. No. 9,630,990, which is a national phase application under 35 U.S.C. § 371 of International Application No. PCT/US2014/030147, filed Mar. 17, 2014, which claims the benefit of U.S. Provisional Patent Application No. 61/800,117, filed Mar. 15, 2013, the entire contents of each of which are incorporated herein by reference.

BACKGROUND OF THE INVENTION

Field of the Invention

The present invention in the field of biochemistry and medicine is directed to methods and composition for increasing p53 protein levels, reducing uPA and uPAR and increasing RAI-1 expression, in fibrotic lung (FL) fibroblasts and reducing their proliferation, and for treating idiopathic pulmonary fibrosis (IPF) using nutlin-3a and peptides.

Description of the Background Art

Idiopathic pulmonary fibrosis (IPF) is a poorly understood progressive and fatal lung disease for which no treatment exists other than lung transplantation (Mason D P et al, Ann Thorac Surg 84: 1121-8, 2007). Median survival of five years after diagnosis is less than 20%. Most forms of interstitial lung diseases and other forms of pulmonary fibrosis are characterized by fibrotic lesions, progressive distortion of alveolar architecture occurs and replacement with fibrotic or scar tissues with excess extracellular matrix (ECM) deposition (American Thoracic Society. Am J Respir Crit Care Med 161: 646-664, 2000; Noble P W et al, Clin Chest Med 25:749-758, 2004; Selman M et al, Ann Intern Med 134: 136-151, 2001). This results in progressive dyspnea and loss of lung function. A hallmark morphological lesion is spatial and temporal heterogeneity incorporating areas of normal lung being directly adjacent to areas of fully established fibrosis, microscopic honeycombing, and areas of evolving fibrosis containing actively proliferating and collagen-producing fibroblasts/myofibroblasts, the so called "fibrotic foci".

IPF is the most common chronic, progressive and fatal interstitial lung disease of unknown etiology with an estimated incidence of 40-50 cases for 100,000 individuals in the United States. Increased fibrotic lung ("FL") fibroblasts (or myofibroblast)) viability, activation, production and deposition of ECM typify IPF lungs (Selman M et al, Expert Opin Emerg Drugs 76:341-62, 2011; Shetty, S et al Am J Respir Cell Mol Biol 75:78-87, 1996; Zhu S et al, Am J Physiol: Lung Cell Mol Physiol 297:L97-108, 2009; Suganuma H et al, Thorax 50:984-9, 1995; American Thoracic Society, supra; Noble P W et al, supra).

Previous work by the present inventors (and others) showed that lung fibroblasts including FL-fibroblasts from the lungs of IPF patients express urokinase-type plasminogen activator (uPA), uPA receptor, (uPAR) and plasminogen activator inhibitor-1 (PAI-1) (Shetty et al, 1996, supra; Shetty S and Idell S. Am J Physiol 274:L871-L882, 1998; Chang W et al, J Biol Chem 255:8196-206, 2010). uPA is mitogenic for both normal lung (NL) and FL-fibroblasts, and the process involves uPA binding to uPAR through the uPA growth factor domain (Tkachuk V et al. Clin Exp Pharmacol Physiol 23:759-65, 1996; Padro T et al, J Cell Sci 775: 1961-71, 2002; Shetty S et al., Am J Physiol 2d5:L972-L982, 1995; Shetty S et al, Antisense Res Dev 5:307-314, 1995). In addition, uPA augments uPAR expression (Shetty S et al, J Biol Chem 276:24549-56, 2001; Shetty S et al, Am J Respir Cell Mol Biol 30:69-75, 2004). Several years ago, the present inventors reported that FL-fibroblasts from IPF lungs express significantly more uPA and uPAR, and show a higher rate of basal and uPA-mediated proliferation than the NL-fibroblasts (Shetty et al, 1996, supra; 1998, supra). Other groups confirmed that increased uPAR expression by FL-fibroblasts from patients with IPF contributes to the migratory behavior (Mace K A et al, J Cell Sci 775:2567-77; 2005; Basire A et al., Thromb Haemost 95:678-88, 2006; Zhu, S. et al, 2009, supra.

Studies by the present inventor and colleagues found that uPA regulates epithelial cell apoptosis/survival through regulation of p53 (Shetty S et al, 2005, supra) which controls reciprocal expression of uPA (Shetty P et al, Am J Resp Cell Mol Biol, 39:364-72, 2008), its receptor uPAR (Shetty S et al. Mol Cell Biol 27:5607-18, 2007) and its major inhibitor PAI-1 (Shetty S et al J Biol. Chem 283: 19570-80, 2008) at the posttranscriptional level and involves a novel cell surface signaling interaction between uPA, uPAR, caveolin-1 ("Cav-1") and βi-integrin (Shetty S et al, 2005, supra). Based on the appreciation of the foregoing, the present inventors conceived of new compositions and methods for treating ALI and its consequent remodeling reactions During lung fibrosis (which term is used interchangeably with "pulmonary" fibrosis), expression of the transcriptional factor p53, known primarily as a tumor suppressor protein, is severely suppressed in fibrotic fibroblasts which in turn induces expression of uPA and uPAR while PAI-1 expression is significantly inhibited. Suppression of PAI-1 expression and concurrent induction of uPA and uPAR expression as a consequence of inhibition of p53 expression fibrotic fibroblasts causes fibroblast proliferation and ECM deposition, i.e., fibrosis. Increased mdm2 interaction with p53 and subsequent mdm2-mediated ubiquitination of p53 contributes to inhibition of p53 in fibrotic fibroblasts.

A reciprocal relationship between the activities of p53 and NF-κB has been demonstrated in cancer cells, but there is little information concerning interactions between p53 and NF-κB in inflammatory processes. Liu G et al (J Immunol. 752:5063-71(2009)) found that neutrophils and macrophages lacking p53. (p53$^{-/-}$) have greater responses to stimulation with bacterial lipopolysaccharide (LPS) than do p53' cells, and they produce greater amounts of proinflammatory cytokines, including TNF-a, IL-6, and MIP-2, and demonstrate enhanced NF-KB DNA-binding activity. p53$^{-/-}$ mice are more susceptible than are p53*$^{-/+}$ mice to LPS-induced acute lung injury (ALI). The enhanced response of p53$^{-/-}$ cells to LPS does not involve alterations in intracellular signaling events associated with engagement of the toll-like receptor TLR4 engagement (e.g., activation of MAP kinases, phosphorylation of IκB-α or the p65 subunit of NF-KB, or degradation of IκB-α. Culture of LPS-stimulated neutrophils and macrophages with nutlin-3 a, attenuated NF-κB DNA-binding activity and production of proinflammatory cytokines. Treatment of mice with nutlin-3a reduced the severity of LPS-induced ALI. The authors concluded that p53 regulates NF-κB activity in inflammatory cells and suggested that modulation of p53 may have potential therapeutic benefits in acute inflammatory conditions such as ALI.

Nutlin (or Nutlin-3a) (Abbreviated NTL)

The chemical structure of the organic molecule 4-2-4,5-dihydro-1H-imidazole-1-piperazin-2-one $C_{30}H_{30}Cl2N4O4$) also termed nutlin or nutlin-3 a is shown below.

Formula 1

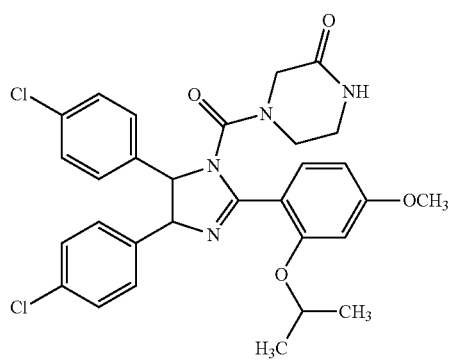

NTL is an antagonist of MDM2, which is a p53 activator and an apoptosis inducer. MDM2 works by binding the p53 tumor suppressor protein and negatively regulating its transcriptional activity and stability. Inhibition of the MDM-p53 interaction results in the stabilization of p53, cell cycle arrest and apoptosis. Nutlin-3 has shown potential as a cancer treatment by activating the p53 pathway in cancer cells. (Tovar, C. et al, Proc Natl Acad Sci USA 103: 1888-1893 (2006); Vassilev, L. T. et al. Science 303 844-848 (2004); El-Deiry, W. S. Cancer J 77:229-236 (1998)).

U.S. Pat. No. 7,893,278 (Haley et al.) disclosed chiral nutlin-3 both generically and specifically. U.S. Pat. No. 6,734,302 describes racemic nutlin-3 The '278 patent teaches a compound of the formula Formula 2

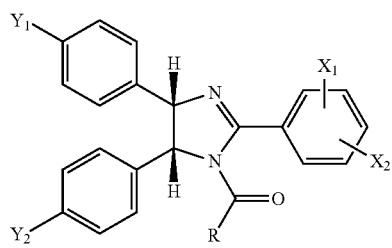

Both of the above patents discuss uses as inhibitors of the Mdm2-p53 interaction and in cancer treatment.

U.S. Pat. Publication 2011/0301142 (Hutchinson et al.) teaches a method of treating idiopathic pulmonary fibrosis in a mammal comprising administering a therapeutically effective amount of a LPA1 receptor antagonist to the mammal. The antagonist may be certain imidazole derivatives but not imidazoline type compounds such as NTL.

U.S. Pat. No. 6,596,744 (Wagle et al.) discloses a method of treating or ameliorating certain fibrotic diseases with heterocyclic compounds, all of which are clearly distinct from NTL. The diseases disclosed include fibrotic lung diseases that have as a manifestation fibrotic hypertrophy or fibrosis of lung tissue. These diseases include pulmonary fibrosis (or interstitial lung disease or interstitial pulmonary fibrosis), idiopathic pulmonary fibrosis, the fibrotic element of pneumoconiosis, pulmonary sarcoidosis, fibrosing alveolitis, the fibrotic or hypertrophic element of cystic fibrosis, chronic obstructive pulmonary disease, adult respiratory distress syndrome and emphysema.

Dey et al. in Cell Cycle 6:2178-85 (2007) describes that nutlins were identified as the first potent and specific small molecule Mdm2 antagonists that inhibit the p53-MDM2 interaction.

None of the foregoing documents disclose treating IPF with nutlin-3 a

Caveolin-1-Derived Peptides

The present inventors discovered that a 20 residue peptide DGIWKASFTTFTVTKYWFYR, (SEQ ID NO:2) which is the scaffolding domain of caveolin-1 (Cav-1; SEQ ID NO:3, shown below) protected lung epithelial cells (LECs) from bleomycin ("BLM")-induced apoptosis vitro and in vivo and prevented subsequent pulmonary fibrosis by attenuating lung epithelial damage (Shetty et al., allowed U.S. patent application Ser. No. 12/398,757 published as U.S. 2009-0227515A1 (Sep. 10, 2009) which is hereby incorporated by reference in its entirety. The present inventors also discovered a 17 residue peptide NYHYLESSMTALYTLGH (SEQ ID NO:4), termed PP 2, also protected LECs from BLM-induced apoptosis in vitro and in vivo and prevented subsequent pulmonary fibrosis by attenuating lung epithelial damage.

Shetty et al, 2009 (supra) also describes biologically active substitution, addition an deletion variants of these peptides as well as peptide multimers and deliverable polypeptides comprising the above peptides, and pharmaceutical compositions comprising the foregoing peptides, variants and multimers. Those compositions inhibit apoptosis of injured or damaged lung epithelial cells and treating acute lung injury and consequent pulmonary fibrosis/IPF.

The foregoing document did not identify a particular fragment of CSP (disclosed below as part of the present invention) termed CSP-4, which has the sequence FTTFTVT (SEQ ID NO: 1) and which has the biological activity of CSP and constitutes part of the subject matter of the present invention.

In view of the poor prognosis and lack of therapeutic approaches for IPF, there is an urgent need for new interventions to reverse or at least slow the progression of disease. This critical therapeutic gap is addressed by the present invention.

The present invention constitutes an extension of the inventor's earlier findings (S. Shetty et al., 2007, 2008 & 2009, supra). As described in the sections below, the p53 regulates the expression of uPA, uPAR and PAI-1. The process involves MDM2-mediated control of p53 protein expression at the posttranslational level without affecting p53 mRNA. These observations demonstrate a causal link between expression of p53 and the uPA-fibrinolytic system in fibrotic repair.

SUMMARY OF THE INVENTION

Inhibition of p53 protein interaction with MDM2 using NTL augments p53 and PAI-1 while inhibiting uPA and uPAR. These changes results in apoptosis of fibrotic fibroblasts and inhibition of proliferation of fibrotic fibroblasts isolated from the lungs of patients with IPF as well as from the lungs of mice with BLM-induced accelerated pulmonary fibrosis.

According to the present invention, NTL Inhibits progressive and established pulmonary fibrosis by inducing or augmenting p53 expression in fibrotic fibroblasts. Therefore, this compound is useful for treating pulmonary fibrosis in a subject in need thereof.

The present inventors conceived that disrupted p53-mediated control of the uPA-fibrinolytic system in FL-fibroblasts is a basis for targeted therapy of IPF. In FL-fibroblasts, baseline expression of p53 and microRNA-34a (miR-34a) are markedly suppressed while the levels of ECM proteins such as collagen-I (Col-I) and a-smooth muscle actin (a-SMA) are increased. Treatment of FL-fibroblasts with either the mdm2 inhibiting compound nutlin-3a or CSP-4 augments p53 and PAI-1 expression with reciprocal inhibition of uPA and uPAR.

Treatment of FL-fibroblasts with nutlin-3a or CSP-4 also inhibits the production of ECM. These preliminary findings and recent publications of the present inventors and colleagues justify an interventional approach to restore cross-talk between the p53 and uPA-fibrinolytic system which is otherwise distorted in FL-fibroblasts leading to lung fibrosis. p53 has pleiotropic effects that go beyond control of uPA-fibrino lytic system[2]. However, PAI-1 is the downstream effector of p53 in fibroblasts and other cells.

Importantly, restoration of p53 in FL-fibroblasts modulates expression of uPA, uPAR and PAI-1, cellular viability and production of ECM. The p53-uPA fibrinolytic system-targeted approach in FL-fibroblasts is illustrated in FIG. 1. p53 induces miR-34a transcription while miR-34a augments acetylation of p53 through inhibition of histone deacetylase sirtuin1 (SIRT1). This leads to stabilization of p53 protein due to inhibition of its degradation mediated by mdm2. However, in FL-fibroblasts, the basal levels of p53 protein and miR-34a are markedly suppressed due to increased ubiquitination of p53 protein by mdm2 as a consequence of low baseline expression of caveolin-1. This leads to reduced p53-mediated inhibition of uPA and uPAR, or concurrent induction of PAI-1. These changes contribute to excessive FL-fibroblast proliferation and production of ECM and are reversed by CSP-4 and nutlin-3a. CSP-4 and nutlin-3a increase p53 levels by inhibiting mdm2-mediated degradation of p53 protein.

Restoration of p53 expression and p53-mediated changes in the uPA-fibrinolytic system in FL-fibroblasts leads to attenuation of viability, and restricts production and deposition of ECM.

Fibrosis is inhibited in BLM-challenged mice with established pulmonary fibrosis via restoration of p53 levels in FL-fibroblasts that in turn suppresses the proliferation signals uPA and uPAR while inducing the pro-apoptotic signal for these cells; PAI-1.

The inventors show, for the first time, that p53-mediated changes of the uPA-fibrinolytic system regulate pro-fibrotic response of lung fibroblasts that are central to the pathogenesis of pulmonary fibrosis and that this pathway can be targeted for therapeutic benefit. Unlike NL-fibroblasts from histologically "normal" lungs, FL-fibroblasts, including fibroblasts/myofibroblasts from fibrotic lung tissues, express very low levels of baseline p53, miR-34a and caveolin-1 while uPA and uPAR expressions are high. Treatment of FL-fibroblasts with CSP-4, or the low molecular weight compound nutlin-3a restore p53 and miR-34a expression, and induce PAI-1. These changes suppress uPA and uPAR expression and inhibit ECM deposition. These agents also reverse BLM-induced pulmonary fibrosis and protect the lung epithelium, which likewise demonstrates crosstalk between p53 and regulation of the fibrinolytic system. Therefore, CSP-4-mediated or nutlin-3a-mediated mitigation of pulmonary fibrosis represent novel therapeutic approaches.

There is currently no effective treatment to reverse lung fibrosis. The present invention addresses this important gap and provides novel compounds and methods for targeting FL-fibroblasts and cross-talk between p53 and the uPA-fibrinolytic system to effectively treat fibrotic lung disease.

The present invention is also directed to compositions of matter. In one embodiment, the composition is a peptide compound that increases p53 protein levels, reduces uPA and increases PAI-1 expression in FL fibroblasts, preferably selected from the group consisting of:
(a) a peptide designated CSP-4 the sequence of which is FTTFTVT (SEQ II) NO: 1);
(b) an additional variant of the CSP-4 peptide of up to about 20 amino acids in length and which is not the scaffolding domain (CSP) of caveolin-1 (Cav-1) having the sequence SEQ ID NO:3;
(c) a covalently-modified chemical derivative of the CSP-4 peptide of (a),
(d) a covalently-modified chemical derivative of the variant of (b),
which variant or chemical derivative has at least 20% of the biological or biochemical activity of the CSP-4 peptide in an in vitro or in vivo assay. The peptide variant, chemical derivative or multimer described above or below preferably has the following activity relative to the activity of CSP-4: at least about 20%, 30%, 40%, 50%, 60%, 65%, 70%, 75%, 80%, 85%, 90%, about 95%, 97%, 99%, and any range derivable therein, such as, for example, from about 70% to about 80%, and more preferably from about 81% to about 90%; or even more preferably, from about 91% to about 99%. The peptide variant chemical derivative or multimer may have 100% or greater than 100% of the activity of CSP-4. This relative activity may be based on any method disclosed herein or known in the art for evaluating such activity.

A preferred compound is the heptapeptide designated CSP-4, FTTFTVT (SEQ ID NO. 1). A preferred peptide multimer comprises at least two monomers, each monomer being the CSP-4 peptide, the variant or the chemical derivative, which multimer:
(a) has the formula $P^1_n$ wherein
(i) $P^1$ is the peptide, variant or chemical derivative as above, and
(ii) n=2-5, or
(b) has the formula $(P^1—X_m)_n—P^2$, wherein
(i) each of $P^1$ and $P^2$ is, independently, the peptide, variant or chemical derivative as above,
(ii) each of $P^1$ and $P^2$ is the same or different peptide, variant or derivative
(iii) X is $C_1$-$C_5$ alkyl, $C_2$-$C_5$ alkenyl, $C_2$-$C_5$ alkynyl, $C_1$-$C_5$ polyether containing up to 4 oxygen atoms;
(iv) m=0 or 1; and
(v) n=1-7,
(c) has the formula $(P^1\text{-Gly}_z)_n\text{-}P^2$, wherein:
(i) each of $P^1$ and $P^2$ is, independently, the peptide, variant or derivative,
(ii) each of $P^1$ and $P^2$ is the same or different peptide or variant or derivative;
(iii) z=0-6; and
(iv) n=1-25,
wherein the peptide multimer preferably has at least 20% of the biological activity of the CSP-4 peptide in an in vitro or in vivo assay.

In another embodiment, the present invention is directed to a deliverable peptide, or polypeptide or peptide multimer composition comprising:
(a) the above peptide, variant, derivative, polypeptide, or multimer, and
(b) a delivery or translocation-molecule or moiety bound thereto or associated or admixed therewith.

Preferred translocation molecules or moieties are described below.

Also provided is an anti-fibrotic pharmaceutical composition comprising:
(a) a pharmaceutically acceptable carrier or excipient and,
(b) as the active ingredient the above peptide, peptide variant, chemical derivative, polypeptide or peptide multimer, optionally in combination with a pharmaceutical composition comprising nutlin-3a (NTL) or a chiral cis-imidazoline analogue of NTL that inhibits MDM2-p53 interaction, which NTL analogue has at least 20% of the biological or biochemical activity of NTL in an in vitro or in vivo assay;

Most preferred is the above peptide-related pharmaceutical composition formulated for injection or lung instillation, whereas the optionally combined NTL or NTL analogue is preferably formulated for injection or oral administration.

The present invention is directed to a method for increasing p53 protein levels, reducing uPA and uPAR and increasing PAI-1 expression in fibrotic lung (FL) fibroblasts, comprising providing to the FL fibroblasts an effective amount of a compound that inhibits MDM2 interaction with p53 protein and MDM2-mediated degradation of p53, wherein the compound is:
(a) NTL or a chiral cis-imidazoline analogue of NTL that inhibits MDM2-p53 interaction;
(b) a peptide selected from the group consisting of:
 (i) CSP-4, the sequence of which is FTTFTVT (SEQ ID NO: 1);
 (ii) an addition variant of the CSP-4 peptide which addition variant does not exceed 20 amino acids in length;
 (iii) a covalently modified chemical derivative of the CSP-4 peptide, or
(c) a peptide multimer comprising at least two monomers each monomer being the CSP-4 peptide, the variant or the chemical derivative of (b), or
(d) a combination of any of (a)-(c)
wherein the NTL analogue, the peptide variant, the peptide chemical derivative or the peptide multimer has at least 20% of the biological or biochemical activity of NTL or the CSP-4 peptide in an in vitro or in vivo assay.

The NTL analogue described above or below preferably has the following activity relative to the activity of NTL: at least about 20%, 30%, 40%, 50%, 60%, 65%, 70%, 75%, 80%, 85%, 90%, about 95%, 97%, 99%, and any range derivable therein, such as, for example, from about 70% to about 80%, and more preferably from about 81% to about 90%; or even more preferably, from about 91% to about 99%. The NTL analogue may have 100% or greater than 100% of the activity of NTL. This relative activity may be based on any method disclosed herein or known in the art for evaluating such activity.

In preferred embodiment of the above method, the compound in the above method is NTL. In another embodiment, the compound is the CSP-4 peptide of SEQ ID NO: 1. In another embodiment of th method, the compound is the peptide multimer, preferably one that comprises monomers of the CSP-4 peptide (SEQ ID NO: 1).

Preferably, when the above method uses a peptide multimer:
(a) the peptide multimer has the formula $P^1_n$ wherein
 (i) $P^1$ is the peptide, variant or chemical derivative as above, and
 (ii) n=2-5, or
(b) the peptide multimer has the formula $(P^1-X_m)_n-P^2$, wherein
 (i) each of $P^1$ and $P^2$ is, independently, the peptide, variant or chemical derivative;
 (ii) each of $P^1$ and $P^2$ is the same or different peptide, variant or derivative;
 (iii) X is $C_1$-$C_5$ alkyl, $C_2$-$C_5$ alkenyl, $C_2$-$C_5$ alkynyl, $C_1$-$C_5$ polyether containing up to 4 oxygen atoms;
 (iv) m=0 or 1; and
 (v) n=1-7, or
(c) the peptide multimer has the formula $(P^1-Gly_z)_n-P^2$, wherein:
 (i) each of $P^1$ and $P^2$ is, independently, the peptide, variant or derivative,
 (ii) each of $P^1$ and $P^2$ is the same or different peptide or variant or derivative;
 (iii) z=0-6; and
 (iv) n=1-25.

Preferably the multimer has at least 20% of the biological activity of the CSP-4 peptide in an in vitro or in vivo assay.

Also provided is a method for treating a mammalian subject, preferably a human, having a disease or condition characterized by pulmonary fibrosis (i.e., IPF), comprising administering to the subject an effective amount of a compound or composition that, by inhibiting MDM2-mediated degradation of p53 protein, increases p53 protein levels, reduces uPA and uPAR levels and increases PAI-1 expression in FL fibroblasts. In a preferred embodiment of this method, the compound or composition is
(a) Nutlin-3a (NTL) or a chiral cis-imidazoline analogue thereof that inhibits MDM2-p53 interaction;
(b) a peptide selected from the group consisting of:
 (i) CSP-4, the sequence of which is FTTFTVT (SEQ II) NO: 1), the most preferred peptide embodiment;
 (ii) an addition variant of the CSP-4 peptide which addition variant does not exceed 20 amino acids in length;
 (iii) a covalently modified chemical derivative of the CSP-4 peptide, or
(c) peptide multimer comprising at least two monomers each monomer being the CSP-4 peptide, the variant or the chemical derivative of (b), most preferably a multimer of CSP-4,
(d) the above deliverable peptide, or polypeptide or peptide multimer composition, or
(e) a combination of any of (a) to (d),
wherein the NTL analogue, or the peptide variant, the peptide derivative or the peptide multimer has at least 20% of the biological or biochemical activity of NTL or the CSP-4 peptide, respectively, in an in vitro or in vivo assay.

In this method, the compound is preferably in a pharmaceutical composition that further comprises a pharmaceutically acceptable carrier or excipient. The compound may be a pharmaceutically acceptable salt of the NTL. NTL analogue or peptide compound. In a preferred embodiment of the method, the compound is NTL. In another embodiment of this method, the compound is the peptide multimer, most preferably a multimer comprising monomers of the CSP-4 peptide FTTFTVT (SEQ ID) NO: 1).

The present invention is also directed to the use of NTL, the above NTL analogue, the above peptide, variant, chemical derivative or multimer for
(a) in increasing p53 protein levels, reducing uPA and increasing PAI-1 expression in FL fibroblasts, or
(b) treating a disease or condition characterized as pulmonary fibrosis.

Also provided is the use of NTL, the above NTL analogue, the above peptide, variant, chemical derivative or peptide multimer as defined herein for the manufacture of a medicament for use in treating a subject having a disease or condition characterized as pulmonary fibrosis.

BRIEF DESCRIPTION OF THE DRAWINGS

FIGS. 3A-3B. Caveolin-1, p53 and PAI are decreased and uPA is increased in human FL(IPF)-fibroblasts from IPF lungs is associated with increased col-I and inhibition of miR-34a. (FIG. 3A) Cell lysates from normal lung (NL)- and FL-fibroblasts were immunoblotted for changes in the proteins. The figure illustrates the typical results of NL-fibroblasts (n=10 cell line) and FL-fibroblasts (n=18 cell lines). (FIG. 3B) Total RNA from NL-(n=3) and FL-(n=4) fibroblasts were tested for miR-34a expression by real-time PCR. Northern blotting of RNA from representative samples using $^{32}$P-labeled antisense probe for miR-34a and the loading control snRNA (U6) are shown at the bottom of the bar.

FIGS. 5A-5D. Differential expression of uPA and PAI-1 by FL-versus NL-fibroblasts from mice. FL-fibroblasts isolated from the lungs of mice 21 days after BLM injury or NL-fibroblasts from control mice exposed to intranasal saline as described elsewhere (Bandhary et ah, 2012, supra). The lysates from NL- and FL-fibroblasts were immunoblotted for changes in the expression of p53, uPA, PAI-1 and col-I proteins (FIG. 5A). Total RNA extracted from mouse lung tissues (FIG. 5B) or from isolated NL- and FL-Fibroblasts (n=6) (FIG. 5C) from the lung tissues of mice with BLM-induced fibrosis or control (saline) mice were tested for uPA, PAI-1 and collagen-I (Col-I) mRNA by quantitative real-time PCR. NL- and FL-fibroblasts from mice were cultured in 12 well plates in DMEM media. After three days fibroblasts were counted to determine the rate of proliferation (FIG. 5D).

FIGS. 6A-6D. CSP (CSP4) augments p53 expression via induction of miR-34a in FL(IPF)-fibroblasts. (FIG. 6A) NL- and FL-fibroblasts (n=3) were treated with PBS, CSP-4 (CSP) or control peptide (CP). RNA was analyzed for miR-34a by real-time PCR. (FIG. 6B) FL-fibroblasts were treated with PBS or CSP or CP with or without miR-34a antisense (miR-34a-AS) or pre-miR-34a or control miRNA (Ctr-miR). Conditioned media (CM) were immunoblotted for PAI-1 and lysates (CL) for p53 and β-actin. (FIG. 6C) FL-fibroblasts were treated with PBS or CSP or CP in the presence or absence of miR-34a-AS, pre-miR-34a or Ctr-miR. RNA was analyzed for changes in miR-34a by real-time PCR. (FIG. 6D) A series of overlapping deletions were made in CSP and these peptides were used to treat FL-fibroblasts with. The peptide sequences were CSP (SEQ ID NO:2), CSP-2: DGIWKAS (SEQ ID NO:12), CSP-3: KYWFYR (SEQ ID NO:13), CSP-4 (SEQ ID NO:1), and CP (SEQ ID NO:5). Changes in p53, uPA, PAI-1 and col-I were later assessed to identify the minimum amino acids required for the CSP effects.

(FIG. 7A) Lysates from NL- and FL-fibroblasts (n=3) were immunoblotted for p53, mdm2 and β-actin. (FIG. 7B) Lysates from NL- and FL-fibroblasts were immunoprecipitated (IP) with anti-mdm2 antibody and immunoblotted (B) for the associated p53 protein.

(FIG. 5A) FL-fibroblasts were exposed to PBS, nutlin-3a (10 uM), CSP-4 (10 nM) or control peptide (CP) for 48 h. The cell lysates were immunoblotted for the expression of Col-I, PAI-1, p53, uPA and β-actin. (FIG. 8B) FL-fibroblasts cultured in 12 well plates in DMEM media were exposed to vehicle (PBS) or nutlin-3a. CSP-4 or CP. After 3 d, cells were detached and counted. (FIG. 8C) FL-fibroblasts were transduced with empty adenovirus vector alone (Ad-EV) or Ad-vector expressing p53 (Ad-p53), PAI-1 (Ad-PAI-1) or caveolin-1 (Ad-Cav-1). After 48 h. cell lysates were immunoblotted for Col-I, p53, PAI-1, uPA and β-actin.

(FIG. 9A): Conditioned medium samples were immunoblotted for PAI-1, uPA, and soluble col-I while cell lysates were tested for p53, a-SMA and β-actin (FIG. 8B). Total RNA isolated from NL-fibroblasts treated with control or p53 shRNA were analyzed for changes in the expression of uPA, PAI-1, col-I and β-actin mRNA by quantitative real-time PCR FIGS. 10A-10D. Nutlin-3a (NTL) inhibits lung fibrosis in BLM-treated mice. Mice were exposed to BLM for 14 d to induce lung fibrosis. Saline treated mice were used as fibrosis controls. After 14 d, mice exposed to BLM were injected IV with either vehicle or nutlin-3 a (10 mg/kg body weight) (Zhang F et al Drug Metab Dispos 39: 15-21, 2011) to determine whether nutlin-3 a inhibited established lung fibrosis. On day 21 after BLM injury, mice underwent CT scanning to assess the extent of fibrosis (FIG. 10A). One representative example is shown (n=9). (FIG. 1013) Lung compliance and resistance were measured in the same mice using the Flexivent system to assess improvement in lung function after nutlin-3 a treatment (n=9).

(FIG. 11B). Lung volumes were measured in the same mice (n=9) using quantitative CT renditions. (FIG. 11C): Lung sections were subjected to trichrome and H&E staining (not shown) to assess collagen deposition as an indicator of lung fibrosis. (FIG. 11D) Analysis of whole lung homogenates for total hydroxyproline content.

(FIG. 12A): Lung sections (d 21 after BLM injury) were subjected to immunohistochemistry (IHC) for Ki-67 to assess proliferation. One representative example is shown (n=9). Fibroblasts were isolated from the lungs of mice exposed to saline, BLM or BLM+nutlin-3a (as described in FIG. 11A) were tested for the changes in expression of col-I, p53 and downstream uPA and PAI-1 proteins by Western blotting (FIG. 12B), and mRNA by quantitative RT-PCR (FIG. 12C).

DESCRIPTION OF THE PREFERRED EMBODIMENTS

Figure 1:
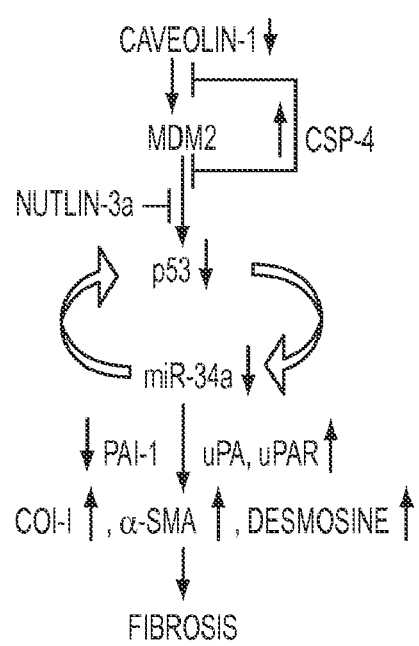
FIG. 1 is a schematic illustration showing that low baseline expression of p53 and deranged p53-mediated control of the uPA-fibrinolytic system in fibrotic lung (FL)-fibroblasts leads to fibrogenesis. The mechanisms of action and pathways involved in IPF and in its treatment by the methods and composition of the present invention are outlined.
Figure 2A:
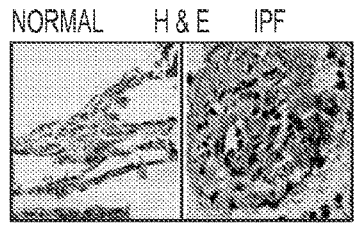
FIGS. 2A-2I. Fibrotic foci in IPF lungs demonstrate deceased FL-fibroblast p53 expression. The lung sections from IPF patients and control "normal" subjects were stained for H&E (FIG. 2A), vimentin (FIG. 2B), trichrome (FIG. 2C), p53 (FIG. 2D), PAI-1 (FIG. 2E), Ki-67 (FIG. 2F), immunofluorescence for PAI-1 and SP-C (FIG. 2G) or p53 and SP-C (FIG. 2H) or p53 and PAI-1 (FIG. 2I). One representative example is shown (n=5 IPF lung specimens).
Figure 2B:
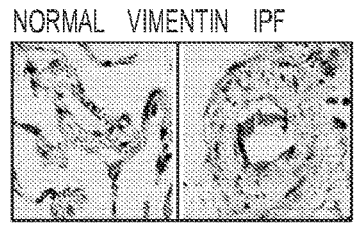
Figure 2C:
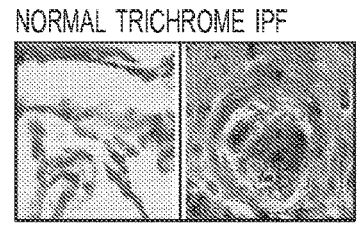
Figure 2D:
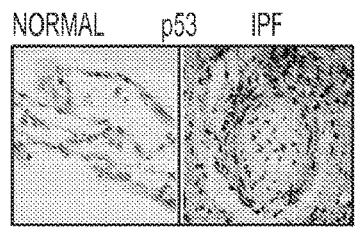
Figure 2E:
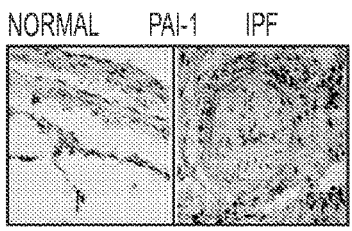
Figure 2F:
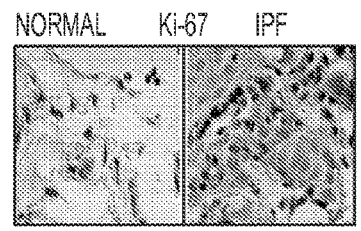
Figure 2G:
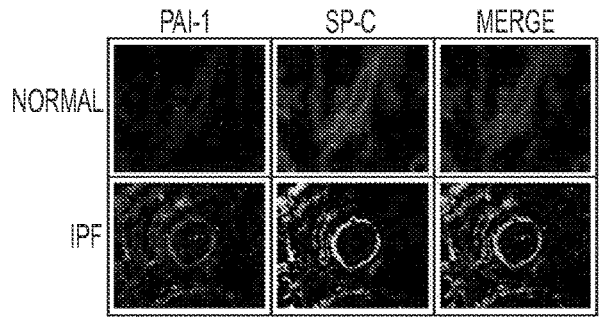
Figure 2H:
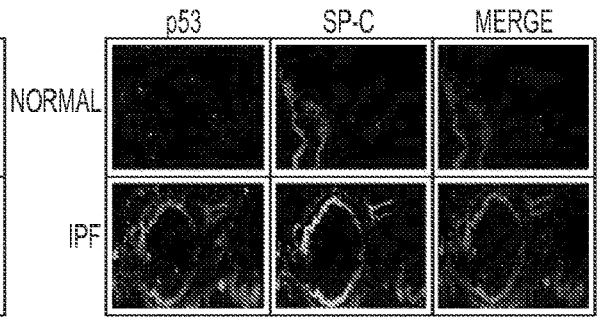
Figure 2I:
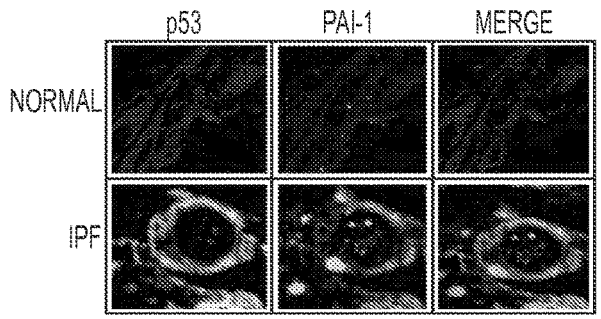

The present inventors discovered that basal expression of "tumor suppressor" protein, p53 and plasminogen activator inhibitor-1 (PAI-1) are markedly reduced in FL-fibroblasts obtained from the lungs of IPF patients. This is also true for mice with BLM-induced accelerated pulmonary fibrosis, an accepted model of human IPF. p53 regulates the expression of major components of uPA-fibrinolytic (uPA, uPAR and PAI-1) system. However, it has been unclear how changes in the levels of these proteins contribute to the pathogenesis of pulmonary fibrosis, and whether restoration of the normal mode of p53-uPA fibrinolytic system cross-talk mitigates lung fibrosis.

According to the present invention, increased uPA and uPAR expression, and a concurrent inhibition of PAI-1 due to a lack of p53 expression in FL-fibroblasts are critical to the development of pulmonary fibrosis. Induction of p53 expression, and restoration of p53-uPA-fibrinolytic system cross-talk through p53-mediated reduction of uPA, and a concurrent increase in PAI-1 expression in FL-fibroblasts, mitigates IPF and is the basis for treating this disease with NTL.

Unlike normal lung ("NL") fibroblasts, fibroblasts obtained from lungs of patients with IPF ("FL"-fibroblasts) or from mice with BLM-induced lung fibrosis express minimal p53. Further, FL-fibroblasts produce low levels of PAI-1, while expression of uPA and uPAR are markedly elevated.

The present invention targets the all three major components (uPA, uPAR and PAI-1) of the uPA-fibrinolytic system in a global and coordinate manner. Concurrently targeting all three major components of the uPA-fibrinolytic system through restoration of p53 expression in FL-fibroblasts mitigates fibrosis.

Accordingly, this treatment affects primary FL-fibroblasts and lung tissue isolated from the patients with IPF ex vivo, and in vivo. These changes were observed in a mouse model with established lung fibrosis in which intermediaries and downstream mediators of the salutary effects of nutlin-3a were defined.

Nutlin-3a

Compounds useful in the method of the present invention include nutlin-3a (also referred to as nutlin and NTL) which is 4-2-4,5-dihydro-1H-imidazole-1-piperazin-2-one $(C_{30}H_{30}Cl_2N_4O_4)$ Formula 1

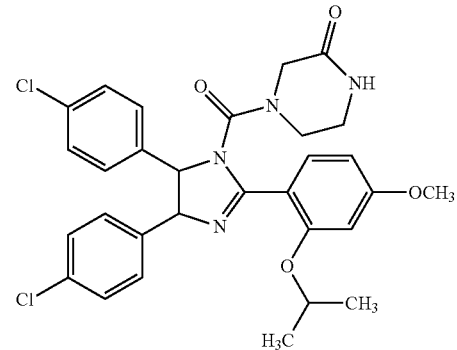

This compound is described in U.S. Pat. No. 7,893,278 (Haley et al), incorporated by reference in its entirety. Also useful in the present invention are a broader genus of chiral cis-imidazoline analogues of NTL that share the property of inhibiting MDM2-p53 interactions. By analogues of NTL is intended the genus of molecules disclosed in the '278 patent, and characterized by Formula 2 below.

Formula 2

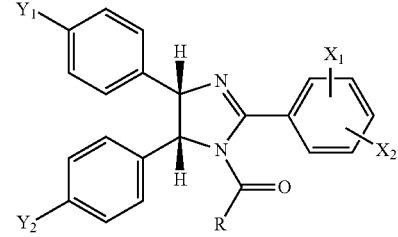

in which

R is selected from saturated and unsaturated 5- and 6-membered rings containing at least one hetero atom, the hetero atom is can be S, N or O The ring can be substituted with a lower alkyl group which alkyl can be further substituted with at least one of —C=O—Ri, —SO$_2$CH$_3$, or —CH$_2$C=OCH$_3$, R$_1$ is selected from the group consisting of H, —NH$_2$, —N-lower alkyl, lower alkyl substituted with a hydroxy, lower alkyl substituted with —NH$_2$, and a 5- or 6-membered saturated ring containing at least one hetero atom (S, N or O);

X$_1$ and X$_2$ are independently selected from the group consisting of H, lower alkoxy, —CH$_2$OCH$_3$, —CH$_2$OCH$_2$CH$_3$, —OCH$_2$CF$_3$ and —OCH$_2$CH$_2$F,

```
  1 MSGGKYVDSE GHLYTVPIRE QGNIYKPNNK AMADELSEKQ VYDAHTKEID LVNRDPKHLN

61 DDVVKIDFED VIAEPEGTHS FDGIWKASFT TFTVTKYWFY RLLSALFGIP MALIWGIYFA

121 ILSFLHIWAV VPCIKSFLIE IQCISRVYSI YVHTVCDPLF EAVGKIFSNV RINLQKEI
```

Yi and Y$_2$ are each independently selected from the group consisting of —CI, —Br, —NO$_2$, —C=N, and —C=CH, and the absolute stereochemistry at the 4 and 5 position of the imidazoline ring is S and R, respectively.

Other compounds that are considered analogues of NTL are compounds of Formula 2 wherein R is piperazinyl substituted with at least one group selected lower alkyl, cycloalkyl, C=ORi, lower alkyl substituted with hydroxy, lower alkyl substituted with —NH$_2$, lower alkyl substituted with —C=ORi. N-lower alkyl, —SO$_2$CH$_3$, =O, —CH$_2$C=OCH$_3$, or piperidinyl substituted with at least one group selected from C1-C3 alkyl, —C1-C2 alkoxy, —C=OCH$_3$, —SO$_2$CH$_3$'—C=O, —OH, —CH$_2$NH$_2$, —C=OCH$_2$NH$_2$, —C=OCH$_2$OH, —C=OCH(OH)CH$_2$OH, —CH$_2$CH(OH)CH$_2$OH, —C=ON(CH$_2$)$_2$, —C=ONH$_2$, and —C=ON(CH$_3$)CH$_3$, —N(CH$_3$)CH$_3$, pyrrolidinyl and piperadinyl.

Also preferred are compounds of formula 2 wherein the XI group at ortho position is selected from lower alkoxy, —OCH$_2$CF$_3$ and —OCH$_2$CH$_2$F, and the X$_2$ group at para position is lower alkoxy. Yet further preferred are compounds wherein the XI group at ortho position is selected from ethoxy, isopropoxy, —OCH$_2$CF$_3$ and —OCH$_2$CH$_2$F, and the X$_2$ group at para position is selected from methoxy and ethoxy.

Further preferred are compounds of Formula 2 wherein R is selected from piperazinyl and substituted piperazinyl. Such compounds are for example: 1-{4-[(4S,5R)-4,5-Bis-(4-chloro-phenyl)-2-(2-isopropoxy-4-methoxy-phenyl)-4,5-dihydro-imidazole-1carbonyl]-piperazin-1-yl}-ethanone; 4-[(4S,5R)-4,5-Bis-(4-chloro-phenyl)-2-(2-isopropoxy-4methoxy-phenyl)-4,5-dihydro-imidazole-1-carbonyl]piperazin-2-one; [(4S,5R)-4,5-Bis-(4-chloro-phenyl)-2-(2-isopropoxy-4-5-methoxy-phenyl)-4,5-dihydro-imidazol-1-yl]-(4-pyrrolidin-1-yl-piperidin-1-yl)-methanone; 4-[(4S,5R)-4,5-Bis-(4-chloro-phenyl)-2-(2-ethoxy-phenyl)-4,5-dihydro-imidazole-1-carbonyl]-piperazin-2one; 1-{4-[(4S,5R)-4,5-Bis-(4-chloro-phenyl)-2-(2-ethoxyphenyl)-4,5-dihydro-imidazole-1-carbonyl]-piperazin-1-yl}-ethanone; 2-{4-[(4S,5R)-4,5-Bis-(4-chloro-phenyl)-2-(2-ethoxyphenyl)-4,5-dihydro-imidazole-1-carbonyl]-piperazin-1-yl}-1-morpholin-4-yl-ethanone; [(4S,5R)-4,5-Bis-(4-chloro-phenyl)-2-(2-ethoxy-phenyl)4,5-dihydro-imidazol-1-yl]-[4-(2-methanesulfonylethyl)-piperazin-1-yl]-methanone; and [(4S,5R)-4,5-Bis-(4-chloro-phenyl)-2-(2-isopropoxy-4-methoxy-phenyl)-4,5-dihydro-imidazol-1-yl]-(4-methyl-piperazin-1-yl)-methanone.

Synthesis of these all molecules is known in the art, some of which is described in the '278 patent.

Peptides Based on the Cav-1 Sequence

The Caveolin-1 (Cav-1) scaffolding domain or peptide (also referred to as CSD or CSP) interferes with Cav-1 interaction with Src kinases mimics the combined effect of uPA and anti-i-integrin antibody as discussed in more detail below. Native human Cav-1 has a length of 178 amino acids and a molecular weight of 22 kDa. The amino acid sequence of Cav-1 is shown below (SEQ ID NO: 3).

CSP is the 20 residue peptide underlined above, and has the sequence GIWKAS FTTFTVTKYWFYR (SEQ II) NO:2) The preferred peptide of the present invention, designated CSP-4 is the fragment FTTFTVT (SEQ ID NO: 1) of CSP and is shown double-underlined within the Cav-1 sequence CSP-4 has the activities shown in the Examples and Figures, below, and affects how p53 regulates LEC viability via coordinate control of uPA, uPAR (upwards) and PAI-1 expression (downwards) and by this presumed mechanism, protect LECs or lung epithelium in vivo from apoptosis and block fibrosis that results from ALL.

In studies disclosed herein, a control peptide for CSP-4, which is termed "CP" is a scrambled peptide with the same amino acid composition as the larger CSP (SEQ ID NO:2), but has a different sequence: WGIDKAFFTT-STVTYKWFRY (SEQ ID NO:5).

Modifications and changes may be made in the structure of CSP-4, and to create molecules with similar or otherwise desirable characteristics. Such functional derivatives or biologically active derivatives (which terms are used interchangeably) are encompassed within the present invention.

Preferred functional derivatives are addition variants and peptide oligomers/multimers, and the like.

These may be generated synthetically but also by recombinant production, and tested for the binding properties or biological activity of CSP-4. A preferred way to measure the activity of the variant is in a competitive binding assay wherein the ability of the peptide variant to compete with binding of soluble caveolin, such as one that is detectably labeled, with soluble uPAR ("suPAR").

It is understood that distinct derivatives of CSP-4 and longer polypeptides comprising CSP-4 may easily be made in accordance with the invention, either by chemical (synthetic) methods or by recombinant means (preferred for longer polypeptides).

Included in within the definition of functional variants of CSP-4 are addition which preferably comprise an additional 1-5 amino acids at either terminus or at both termini. In other embodiments (which are intended to be distinct from the peptide multimers discussed below), further additional residues may be added, up to about 20 residues. In the addition variant of CSP-4, the additional residues N-terminal to, and/or C-terminal to SEQ ID NO: 1 (the core CSP-4 peptide) may include some of those in the order in which they occur in the native sequence in Cav-1 (SEQ ID) NO:4. However, the addition variant cannot be SEQ ID NO:3. Alternatively, other amino acids can be added at either terminus of SEQ ID NO: 1, with the understanding that the addition variant maintains the biological activity and binding activity of CSP-4 (at least 20% of the activity, or preferably greater, as is set forth below).

Preferred substitutions variants of CSP-4 is a conservative substitutions in which 1, 2 or 3 residues have been substituted by different residue. For a detailed description of an protein chemistry and structure, see Schultz G. E. et al, Principles of Protein Structure, Springer-Verlag, New York, 1979, and Creighton, T. E., Proteins: Structure and Molecular Properties, $2^{nd}$ ed., W.H. Freeman & Co., San Francisco, 1993, which are hereby incorporated by reference. Conservative substitutions and are defined herein as exchanges within one of the following groups:

Phe may be substituted by a large aromatic residue: Tyr, Trp.

Thr may be substituted by a small aliphatic, nonpolar or slightly polar residues. e.g., Ala, Ser, or Gly.

Val may be substituted by a large aliphatic, nonpolar residues. Met, Leu, He, Cys.

Even when it is difficult to predict the exact effect of a substitution in advance of doing so, one skilled in the art will appreciate that the effect can be evaluated by routine screening assays, preferably the biological and biochemical assays described herein. The activity of a cell lysate or purified polypeptide or peptide variant is screened in a suitable screening assay for the desired characteristic.

In addition to the 20 "standard" L-amino acids, D-amino acids or non-standard, modified or unusual amino acids which are well-defined in the art are also contemplated for use in the present invention. These include, for example, include β-alanine (β-Ala) and other ω-amino acids such as 3-aminopropionic acid, 2,3-diaminopropionic acid (Dpr), 4-aminobutyric acid and so forth; a-aminoisobutyric acid (Aib); ε-aminohexanoic acid (Aha); δ-aminovaleric acid (Ava); N-methylglycine or sarcosine (MeGly), ornithine (Orn); citrulline (Cit), t-butylalanine (t-BuA); t-butylglycine (t-BuG); N-methylisoleucine (MeIle); phenylglycine (Phg); norleucine (Me); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamnine (Pen); 1,2,3,4-tetrahydroisoquinoline-3-carboxylic acid (Tic); homoarginine (hArg); N-acetyl lysine (AcLys); 2,4-diaminobutyric acid (Dbu), 2,4-diaminobutyric acid (Dab); p-aminophenylalanine (Phe(pNH$_2$)); N-methyl valine (MeVal); homocysteine (hCys), homophenylalanine (hPhe) and homoserine (hSer), hydroxyproline (Hyp), homoproline (hPro), N-methylated amino acids and peptoids (N-substituted glycines).

Other compounds may be designed by rational drug design to function in manner similar to CSP-4. The goal of rational drug design is to produce structural analogs of biologically active compounds. By creating such analogs, it is possible to produce drugs that are more active or more stable than the natural molecules (i.e., peptides), lower susceptibility to alterations which affect functions. One approach is to generate a three-dimensional structure of CSP-4 for example, by NMR or X-ray crystallography, computer modeling or by a combination. An alternative approach is to replace randomly functional groups in the CSP-4 sequence, and determine the affect on function.

Moreover, a biologically active derivative has the activity of CSP-4 in an in vitro or in vivo assay of binding or of biological activity, such as assays described herein. Preferably the polypeptide inhibits or prevents apoptosis of LE-C$_5$ induced by BLM in vitro or in vivo with activity at least about 20% of the activity of CSP-4, or at least about 30%, 40%, 50%, 60%, 65%, 70%, 75%, 80%, 85%, 90%, about 95%, 97%, 99%, and any range derivable therein, such as, for example, from about 70% to about 80%, and more preferably from about 81% to about 90%; or even more preferably, from about 91% to about 99%. The derivative may have 100% or even greater activity than CSP-4.

The peptide may be capped at its N and C termini with an acyl (abbreviated "Ac")- and an amido (abbreviated "Am") group, respectively, for example acetyl (CH$_3$CO—) at the N terminus and amido (—NH$_2$) at the C terminus. A broad range of N-terminal capping functions, preferably in a linkage to the terminal amino group, is contemplated, for example: formyl;

alkanoyl, having from 1 to 10 carbon atoms, such as acetyl, propionyl, butyryl;

alkenoyl, having from 1 to 10 carbon atoms, such as hex-3-enoyl;

alkynoyl, having from 1 to 10 carbon atoms, such as hex-5-ynoyl;

aroyl, such as benzoyl or 1-naphthoyl;

heteroaroyl, such as 3-pyrroyl or 4-quinoloyl;

alkylsulfonyl, such as methanesulfonyl;

arylsulfonyl, such as benzenesulfonyl or sulfanilyl;

heteroarylsulfonyl, such as pyridine-4-sulfonyl;

substituted alkanoyl, having from 1 to 10 carbon atoms, such as 4-aminobutyryl;

substituted alkenoyl, having from 1 to 10 carbon atoms, such as 6-hydroxy-hex-3-enoyl;

substituted alkynoyl, having from 1 to 10 carbon atoms, such as 3-hydroxy-hex-5-ynoyl;

substituted aroyl, such as 4-chlorobenzoyl or 8-hydroxy-naphth-2-oyl;

substituted heteroaroyl, such as 2,4-dioxo-1,2,3,4-tetrahydro-3-methyl-quinazolin-6-oyl;

substituted alkylsulfonyl, such as 2-aminoethanesulfonyl;

substituted arylsulfonyl, such as 5-dimethylamino-1-naphthalenesulfonyl;

substituted heteroarylsulfonyl, such as 1-methoxy-6-isoquinolinesulfonyl;

carbamoyl or thiocarbamoyl;

substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl;

substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function can either be in an amide or ester bond with the terminal carboxyl. Capping functions that provide for an amide bond are designated as NR$^1$R$^2$ wherein R$^1$ and R$^2$ may be independently drawn from the following group: hydrogen;

alkyl, preferably having from 1 to 10 carbon atoms, such as methyl, ethyl, isopropyl;

alkenyl, preferably having from 2 to 10 carbon atoms, such as prop-2-enyl;

alkynyl, preferably having from 2 to 10 carbon atoms, such as prop-2-ynyl;

substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;

substituted alkenyl having from 2 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl;

substituted alkynyl having from 2 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl;

aroylalkyl having up to 10 carbon atoms, such as phenacyl or 2-benzoylethyl;

aryl, such as phenyl or 1-naphthyl;

heteroaryl, such as 4-quinolyl;

alkanoyl having from 1 to 10 carbon atoms, such as acetyl or butyryl;

aroyl, such as benzoyl;

heteroaroyl, such as 3-quinoloyl;

OR' or NR'R" where R' and R" are independently hydrogen, alkyl, aryl, heteroaryl, acyl, aroyl, sulfonyl, sulfinyl, or $SO_2$—R''' or SO—R''' where R''' is substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroaralkyloxy; substituted alkoxy; substituted aryloxy; substituted heteroaryloxy; substituted aralkyloxy, or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard H, Ed: Design of Prodrugs, Elsevier. Amsterdam, 1985).

Judicious choice of capping groups allows the addition of other activities on the peptide. For example, the presence of a sulfhydryl group linked to the N- or C-terminal cap will permit conjugation of the derivatized peptide to other molecules.

Chemical Derivatives of CSP-4

In addition to the capping groups described above which are considered "chemical derivatives" of CSP-4, the preferred chemical derivatives of CSP-4 may contain additional chemical moieties not normally a part of a protein or peptide which can be introduced to CSP-4 or an addition variant of CSP-4 by known means to constitute the chemical derivative as defined herein. Covalent modifications of the peptide are included within the scope of this invention. Such derivatized moieties may improve the solubility, absorption, biological half life, and the like. Moieties capable of mediating such effects are disclosed, for example. Gennaro, A R, Remington: The Science and Practice of Pharmacy. Lippincott Williams & Wilkins Publishers, $21^{st}$ Ed, 2005 (or latest edition)

Such modifications may be introduced into the molecule by reacting targeted amino acid residues of the peptide with an organic derivatizing agent that is capable of reacting with selected side chains or terminal residues. Another modification is cyclization of the peptide—which is generally accomplished by adding terminal Cys residues which can be bonded via a disulfide bond to generate the cyclic peptide. Alternative, a cross-linkable Lys (K) is added at one terminus and a Glu (E) at the other terminus.

Cysteinyl residues (added, e.g., for cyclizing purposes) most commonly are reacted with a-haloacetates (and corresponding amines) to give carboxymethyl or carboxyamidomethyl derivatives. Cysteinyl residues also are derivatized by reaction with bromotrifluoroacetone, a-bromo-P-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitro-phenol, or chloro-7-nitrobenzo-2-oxa-1,3-diazole.

Added lysinyl residues (e.g., for cyclizing) and the amino terminal residue can be derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate, pyridoxal phosphate; pyridoxal; chloroborohydride; trinitrobenzenesulfonic acid, O-methylisourea; 2,4 pentanedione; and transaminase-catalyzed reaction with glyoxylate.

Derivatization with bifunctional agents is useful for cross-linking the peptide or oligomer or multimer to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4, 195, 128; 4,247,642; 4,229,537; and 4,330,440 are employed for protein immobilization.

Other modifications include hydroxylation lysine, phosphorylation of the hydroxyl groups of threonyl residues, methylation of the a-amino groups of side chains of (added) lysine residues chains (Creighton, supra), acetylation of the N-terminal amine, and, in some instances, amidation of the C-terminal carboxyl groups. Also included are peptides wherein one or more D-amino acids are substituted for one or more L-amino acids.

Multimeric or Oligomeric Peptides

The present invention also includes longer peptides built from repeating units of CSP-4 or a functional derivative thereof that has the anti-apoptotic and protective activity of CSP-4. The preferred peptide unit of such a multimer is FTTFTVT (SEQ ID NO: 1). Addition variants of this peptide that may be the "unit" of the multimer preferably include from 1-4 additional amino acids.

A peptide multimer may comprise different combinations of peptide monomers (which may include either or both of SEQ ID NO: 1 or addition variants thereof or a chemically derivatized form of the peptide. Such oligomeric or multimeric peptides can be made by chemical synthesis or by recombinant DNA techniques as discussed herein. When produced by chemical synthesis, the oligomers preferably have from 2-5 repeats of a core peptide sequence, and the total number of amino acids in the multimer should not exceed about 160 residues, preferably not more than 100 residues (or their equivalents, when including linkers or spacers).

A preferred synthetic chemical peptide multimer has the formula $$P^1_n$$

wherein the core peptide $P^1$ is SEQ ID NO: 1, and wherein n=2-5, and wherein the core peptide alone or in oligo- or multimeric form has the biological activity of CSP-4 as disclosed herein in an in vitro or in vivo bioassay of such activity.

In another embodiment, a preferred synthetic chemical peptide multimer has the formula $$(P^1-X_m)_n-P^2$$

$P^1$ and $P^2$ are the core peptides described above, including additional variants, wherein
(a) $P^1$ and $P^2$ may be the same or different; moreover, each occurrence of $P^1$ in the multimer may be a different peptide (or variant);
(b) X is a spacer which comprises or consists of:
  (i) a short organic chain, preferably $C_1$-$C_5$ alkyl, $C_2$-$C_5$ alkenyl, $C_2$-$C_5$ alkynyl, $C_1$-$C_5$ polyether containing up to 4 oxygen atoms, wherein m=0 or 1 and n=1-7; or
  (ii) $Gly_z$ wherein, z=1-6,
and wherein the core peptide alone or in multimeric form has the biological activity of CSP-4 as disclosed herein in an in vitro or in vivo assay of such activity.

When produced recombinantly, a preferred spacer is $Gly_z$, as described above, where z=1-6, and the multimers may have as many repeats of the core peptide sequence as the expression system permits, for example from two to about 25 repeats. A preferred recombinantly produced peptide multimer has the formula:

$$(P^1\text{-}Gly_z)_n\text{-}P^2$$

wherein:
(a) $P^1$ and $P^2$ are, independently, SEQ ID NO: 1 or 3 or an addition variant or derivatized form thereof, wherein $P^1$ and $P^2$ may be the same or different; moreover, each occurrence of $P^1$ in the multimer may be a different peptide (or variant), wherein
  n=1-25 and z=0-6; (preferred ranges of n include n=1-5, 1-10, 1-15, or 1-20) and wherein the core peptide alone or in multimeric form has the biological activity of CSP-4 as disclosed herein in an in vitro or in vivo bioassay of such activity.

In the present peptide multimers, either $P^1$ or $P^2$ is preferably SEQ ID) NO: 1 or an addition variant or chemical derivative thereof. The multimer is optionally capped. It is understood that such multimers may be built from any of the peptides or variants described herein. It is also understood that the peptide multimer should be different from SEQ ID NO: 3 (i.e., not native human Cav-1 and is preferably not a native mammalian Cav-1 homologue).

Peptidomimetics

Also included within the scope of this invention is a peptidomimetic compound which mimics the biological effects of CSP-4. A peptidomimetic agent may be an unnatural peptide or a non-peptide agent that recreates the stereospatial properties of the binding elements of CSP-4 such that it has the binding activity and biological activity of CSP-4. Similar to a biologically active CSP-4 peptide, peptide multimer, a peptidomimetic will have a binding face (which interacts with any ligand to which CSP-4 binds) and a non-binding face. Again, similar to CSP-4, the non-binding face of a peptidomimetic will contain functional groups which can be modified by coupling various therapeutic moieties without modifying the binding face of the peptidomimetic. A preferred embodiment of a peptidomimetic would contain an aniline on the non-binding face of the molecule. The NH¾-group of an aniline has a pKa~4.5 and could therefore be modified by any NH¾-selective reagent without modifying any NH¾ functional groups on the binding face of the peptidomimetic. Other peptidomimetics may not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic moiety could also be directly incorporated during the synthesis of a peptidomimetic and preferentially be displayed on the non-binding face of the molecule.

This invention also includes compounds that retain partial peptide characteristics. For example, any proteolytically unstable bond within a peptide of the invention could be selectively replaced by a non-peptidic element such as an isostere (-methylation; D-amino acid) or a reduced peptide bond while the rest of the molecule retains its peptidic nature.

Peptidomimetic compounds, either agonists, substrates or inhibitors, have been described for a number of bioactive peptides/polypeptides such as opioid peptides. VIP, thrombin, HIV protease, etc. Methods for designing and preparing peptidomimetic compounds are known in the art (Hruby, V J, Biopofymers 33: 1073-1082 (1993); Wiley, R A et al, Med. Res Rev. 73:327-384 (1993); Moore et al. Adv. in Pharmacol 33:91-141 (1995); Giannis et al, Adv. in Drug Res. 29: 1-78 (1997) Certain mimetics that mimic secondary structure are described in Johnson et al, In: Biotechnology and Pharmacy, Pezzuto et al, Chapman and Hall (Eds.), NY, 1993. These methods are used to make peptidomimetics that possess at least the binding capacity and specificity of the CSP-4 peptide and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the three-dimensional structure of a peptide of the invention either free or bound in complex with a ligand (e.g., soluble uPAR or a fragment thereof). Alternatively, the structure of a peptide of the invention bound to its ligand can be gained by the techniques of nuclear magnetic resonance spectroscopy. Greater knowledge of the stereochemistry of the interaction of the peptide with its ligand or receptor will permit the rational design of such peptidomimetic agents. The structure of a peptide or polypeptide of the invention in the absence of ligand could also provide a scaffold for the design of mimetic molecules Deliverable Peptides and Peptide Multimers One embodiment of the invention comprises a method of introducing the peptide of the invention into animal cells, such as human cells. Compositions useful for this method, referred to as "deliverable" or "cell-deliverable" or "cell-targeted" peptides or polypeptides comprise a biologically active peptide according to the invention, preferably CSP-4, or a functional derivative thereof, or a peptide multimer thereof, that has attached thereto or is associated with, a further component which serves as an "internalization sequence" or cellular delivery system. The term "associated with" may include chemically bonded or coupled to, whether by covalent or other bonds or forces, or combined with, as in a mixture. As used herein, "delivery' refers to internalizing a peptide/polypeptide in a cell, Delivery molecules contemplated herein include peptides/polypeptides used by others to effect cellular entry. See for example, Morris et al, Nature Biotechnology, 19: 1173-6, 2001). A preferred strategy is as follows: an apoptosis-inhibiting ("biologically active") peptide of the invention is bonded to or mixed with a specially designed peptide which facilitates its entry into cells, preferably human cells. This delivery system does not require the delivery peptide to be fused or chemically coupled to biologically active peptide or polypeptide (although that is preferred), nor does biologically active peptide or polypeptide have to be denatured prior to the delivery or internalization process. A disadvantage of earlier delivery systems is the requirement for denaturation of the "payload" protein prior to delivery and subsequent intracellular renaturation. These embodiments are based on known approaches for promoting protein translocation into cells.

One type of "delivery" peptide/polypeptide which promotes translocation/internalization includes the HIV-TAT protein (Frankel, A D et al, Cell 55: 1189-93 (1998), and the third a helix from the Antennapedia homeodomain (Derossi et al, J. Biol Chem. 269: 10444-50 (1994); Lindgren, M et al, Trends Pharm. Sci. 27:99-103 (2000), Lindgren et al, Bioconjug Chem. (2000); Maniti O et al, PLoS ONE 5e15819 (2010). The latter peptide, also known as "penetratin" is a 16-amino acid peptide with the wild-type sequence RQI KIWFQN RRMKWKK (SEQ ID NO:6) or two analogues/variants designated W48F (RQI KI FFQNRRMKWKK, SEQ ID NO:7) and W56F (RQI KIWFQNRRMKFKK, SEQ ID NO:8) (Christiaens B et al, Eur J Biochem 2002, 269:2918-2926). Another variant with both of the above mutations is RQIKI FFQNRRMKFKK (SEQ ID NO:9). Transportan, a cell-penetrating peptide is a 27 amino acid-long peptide containing 12 functional amino acids from the N-terminus of the neuropeptide galanin linked by an added Lys residue to the sequence of mastoparan (Pooga, M et al, FASEB J. 12:67-77 (1998)). The sequence of transportan is GWTLN SAGYL LGKIN L KALAALAKKI L (SEQ ID NO: 10) Analogues of penetratin and transportan are described by Lindgren et al, Bioconjug Chem. 2000.

Another protein (family) includes VP22, a herpes simplex virus protein that has the remarkable property of intercellular transport and distributes a protein to many surrounding cells (Elliott, G et al, 1997, Cell 55:223-33, O'Hare et al, U.S. Pat. No. 6,017,735). For example, VP22 linked to p53 (Phelan, A. et al, 1998. Nat Biotechnol 16:440-3) or thymidine kinase (Dilber, M S et al, 1999, Gene Ther 6:12-21) facilitating the spread of linked proteins to surrounding cells in vitro. Also useful are VP22 homologues in other herpes viruses, such as the avian Marek's Disease Virus (MDV) protein UL4A9, that shares homology with HSV-1 VP22 (Koptidesova et al, 1995, Arch Virol. 140:355-62) and has been shown to be capable of intercellular transport after exogenous application (Dorange et al, 2000, J Gen Virol. 81: 2219). All these proteins share the property of intercellular spread that provide an approach for enhancing cellular uptake of the peptides, variants, and multimers of this invention.

Also included are "functional derivatives" of the above intercellular spreading or "delivery" "delivery" or "internalization" proteins and peptides such as HIV-TAT or VP22 which include homologous amino acid substitution variants, fragments or chemical derivatives, which terms are herein for the biologically active peptides. A functional derivative retains measurable translocation or intercellular spreading (VP22-like) activity that promotes entry of the desired polypeptide, which promotes the utility of the present biologically active peptide e.g., for therapy. "Functional derivatives" encompass variants (preferably conservative substitution variants) and fragments regardless of whether the terms are used in the conjunctive or the alternative.

Because the above transport proteins are said to work best when conjugated or otherwise bound to the peptide they are transporting, such as CSP-4 or a variant or multimer thereof, there are a number of disadvantages to using them. A more effective delivery polypeptide that can be admixed with the biologically active peptide and does not need to be chemically bonded for its action is described in Morris et al., supra, as "Pep-1" which has the amphipathic amino acid sequence KETWWETWWTEWSQPKKKRKV (SEQ ID NO:11). Pep-1 consists of three domains:

(1) a hydrophobic Trp-rich motif containing five Trp residues KETWWETWWTEW (residues 1-12 of SEQ ID NO: 11, above). This motif is desirable, or required, for efficient targeting to cell membrane and for entering into hydrophobic interactions with proteins;

(2) a hydrophilic Lys-rich domain KKKRKV (the 6 C-terminal residues of SEQ ID NO: 11) which is derived from the nuclear localization sequence of SV40 virus large T antigen, and improves intracellular delivery and peptide solubility; and (3) a spacer "domain" SQP (3 internal residues of SEQ ID NO: 11) which separate the two active domains above and include a Pro that improves flexibility and integrity of both the hydrophobic and hydrophilic domains.

Accordingly, another embodiment of the invention is a deliverable peptide or polypeptide comprising CSP-4 or a functional derivative thereof as described above, and a delivery or translocation-molecule or moiety bound thereto or associated therewith. The delivery molecule may be a peptide or polypeptide, e.g., (a) HIV-TAT protein or a translocationally active derivative thereof,
(b) penetratin having the sequence RQIKIWFQNRRMKWKK (SEQ ID NO:8),
(c) a penetratin variant W48F having the sequence RQIKIFFQNRRMKWKK (SEQ ID NO:7)
(d) a penetratin variant W56F having the sequence RQIKIWFQNRRMKFKK, SEQ ID NO: 14)
(e) a penetratin variant having the sequence RQIKIWFQNRRMKFKK, SEQ ID NO: 14)
(f) transportan having the sequence GWTLNSAGYLLGKINLKALAALAKKIL (SEQ ID NO:10)
(g) herpes simplex virus protein VP22 or a translocationally-active homologue thereof from a different herpes virus such as MDV protein UL49; or
(h) Pep-1, having the sequence KETWWETWWTEWSQPKKKRKV (SEQ ID NO:11).

When a delivery moiety, such as the peptides and proteins discussed above, is conjugated or fused to the biologically active peptide of the invention, it is preferred that the delivery moiety is N-terminal to the biologically active peptide.

In Vitro Testing of Compositions

The compounds of this invention are tested for their biological activity, e.g., anti-fibrotic activity, their ability to affect expression of uPA, uPAR and PAI-1 mRNAs, inhibit proliferation of lung fibroblasts, etc. using any one of the assays described and/or exemplified herein or others well-known in the art.

In Vivo Testing of Compositions

The ability of a compound (such as a NTL analogues or CSP-4 variants or derivative or peptide multimers to inhibit lung fibrosis in BLM-treated mice is a preferred test for assessing the functional activity of the compound. Other tests known in the art that measure the same type of activity may also be used.

Method of Preventing or Treating Lung Injury and Fibrosis

The compounds and compositions described herein are used in method to inhibits MDM2 interaction with p53 protein in vitro or in vivo, and to treat diseases or conditions associated with ALI and pulmonary fibrosis/IPF.

Pharmaceutical and Therapeutic Compositions and their Administration

The compounds that may be employed in the pharmaceutical compositions of the invention include NTL, and all of the peptide compounds described above, as well as the pharmaceutically acceptable salts of these compounds. "Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et ah, Pharmaceutical Dosage Forms and Drug Delivery Systems ($6^{th}$ Ed. 1995) at pp. 196 and 1456-1457.

As stated above, the compounds of the invention possess the ability to inhibits MDM2 interaction with p53 protein and are exploited in the treatment of acute lung injury and, in particular, pulmonary fibrosis.

The compounds of the invention, as well as the pharmaceutically acceptable salts thereof, may be incorporated into convenient dosage forms, such as capsules, impregnated wafers, tablets or preferably, injectable preparations. Solid or liquid pharmaceutically acceptable carriers may be employed. "Pharmaceutically acceptable," such as pharmaceutically acceptable carrier, excipient, etc., means pharmacologically acceptable and substantially non-toxic to the subject to which the particular compound is administered.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension A summary of such pharmaceutical compositions may be found, for example, in Gennaro, A R, Remington: The Science and Practice of Pharmacy, Lippincott Williams & Wilkins Publishers; $21^{st}$ Ed, 2005 (or latest edition).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the treatment of any of a number of animal genera and species, and are equally applicable in the practice of human or veterinary medicine. Thus, the pharmaceutical compositions can be used to treat domestic and commercial animals, including birds and more preferably mammals, most preferably humans.

The term "systemic administration" refers to administration of a composition or agent such as NTL or the peptides described herein, in a manner that results in the introduction of the composition into the subject's circulatory system or otherwise permits its spread throughout the body, such as intravenous (i.v.) injection or infusion. "Regional" administration refers to administration into a specific, and somewhat more limited, anatomical space, such as instillation in the lung, the preferred route, or intrapleural, intraperitoneal, intrathecal, subdural, or to a specific organ. Other examples include intranasal, which is one route that corresponds to instillation in the lungs, intrabronchial, intra-aural or intraocular, etc. The term "local administration" refers to administration of a composition or drug into a limited, or circumscribed, anatomic space, such as subcutaneous (s.c.) injections, intramuscular (i.m.) injections. One of skill in the art would understand that local administration or regional administration often also result in entry of a composition into the circulatory system. i.e., so that s.c. or i.m. are also routes for systemic administration. Instillable, injectable or infusible preparations can be prepared in conventional forms, either as solutions or suspensions, solid forms suitable for solution or suspension in liquid prior to injection or infusion, or as emulsions. Though the preferred regional routes of administration are into the lungs, the pharmaceutical composition may be administered systemically or topically or transdermally either separately from, or concurrently with, instillation into the lungs.

Other pharmaceutically acceptable carriers for compositions of the present invention are liposomes, pharmaceutical compositions in which the active polypeptide is contained either dispersed or variously present in corpuscles consisting of aqueous concentric layers adherent to lipidic layers. The active polypeptide is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature Those skilled in the art will appreciate other suitable embodiments of the present liposomal formulations.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired.

Therapeutic Methods

The methods of this invention may be used to treat pulmonary fibrosis or IPF in a subject in need thereof. The term "treating" is defined broadly to include, at least the following: inhibit, reduce, ameliorate, prevent, reduce the occurrence or recurrence, including the frequency and/or time to recurrence, or the severity of symptoms of the disease or condition being treated or prevented. This may occur as a result of inhibiting epithelial cell death, inhibiting fibroblast proliferation, any of the other biological or biochemical mechanisms disclosed herein as being associated with or responsible for IPF.

The NTL, NTL analogue, or peptide or peptide derivative or pharmaceutically acceptable salt thereof is preferably administered in the form of a pharmaceutical composition as described above.

Doses of the compound preferably include pharmaceutical dosage units comprising an effective amount of the NTL or peptide. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects.

By an effective amount is meant an amount sufficient to achieve a regional concentration or a steady state concentration in vivo which results in a measurable reduction in any relevant parameter of disease.

The amount of active compound to be administered depends on the NTL, NTL derivative, peptide or derivative thereof selected, the precise disease or condition, the route of administration, the health and weight of the recipient, the existence of other concurrent treatment, if any, the frequency of treatment, the nature of the effect desired, and the judgment of the skilled practitioner.

A preferred single dose, given once daily for treating a subject, preferably a mammal, more preferably human who his suffering from or susceptible to IPF resulting therefrom is between about 0.2 mg/kg and about 250 mg/kg, preferably between about 10 mg/kg and about 50 mg/kg, for example, via instillation (by inhalation). Such a dose can be administered daily for anywhere from about 3 days to one or more weeks. Chronic administration is also possible, though the dose may need to be adjusted downward as is well-understood in the art. The foregoing ranges are, however, suggestive, as the number of variables in an individual treatment regime is large, and considerable excursions from these preferred values are expected.

For continuous administration, e.g., by a pump system such as an osmotic pump that was used in some of the experiments described below, a total dosage for a time course of about 1-2 weeks is preferably in the range of 1 mg/kg to 1 g/kg, preferably 20-300 mg/kg, more preferably 50-200 mg/kg. After such a continuous dosing regiment, the total concentration of the active compound is preferably in the range of about 0.5 to about 50 µM, preferably about 1 to about 10 µM.

An effective concentration of the active compound for inhibiting or preventing inhibiting apoptosis in vitro is in the range of about 0.5 nM to about 100 nM, more preferably from about 2 nM to about 20 nM. Effective doses and optimal dose ranges may be determined in vitro using the methods described herein.

Having now generally described the invention, the same will be more readily understood through reference to the following examples which are provided by way of illustration, and are not intended to be limiting of the present invention, unless specified. The examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Deceased FL-Fibroblast p53 Expression in Fibrotic Foci of IPF Lungs

Staining of lung sections from IPF patients and control "normal" subjects with various reagents, including by immunohistochemistry (IHC) (see FIGS. 2A-2I) revealed that IPF tissues display fibrotic foci which are dense with ECM. FL-fibroblasts dispersed in the vimentin-rich foci showed minimal staining for p53 and PAI-1 antigens. However, immunofluorescence staining for SP-C, PAI-1, p53 and active caspase-3 (not shown) demonstrated that alveolar type II (ATII) cells surrounding the fibrotic foci show elevated staining for p53 and PAI-1 antigens, and are positive for active caspase-3, indicating apoptosis of encircling ATII cells. The IHC results reveal that ATII cells encasing fibrotic foci continuously die due to increased expression of p53 and PAI-1. These wounds are replaced by activated fibroblasts which show minimal basal p53 and PAI-1, and elevated ki-67 staining indicating proliferation due to suppression of p53 and PAI-1 expression.

Example II

Figure 3A:
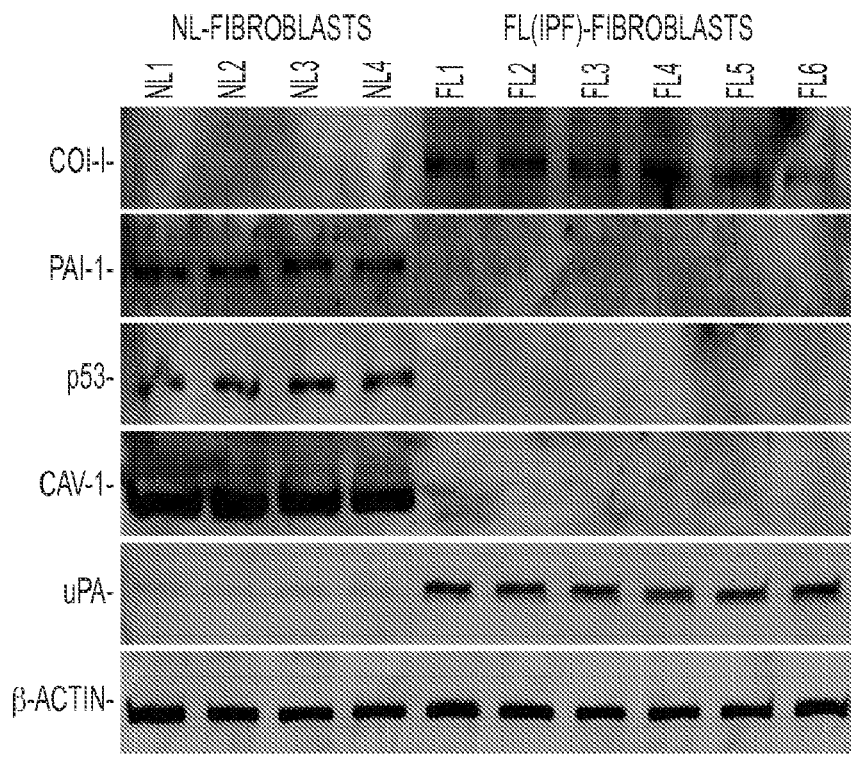
Figure 3B:
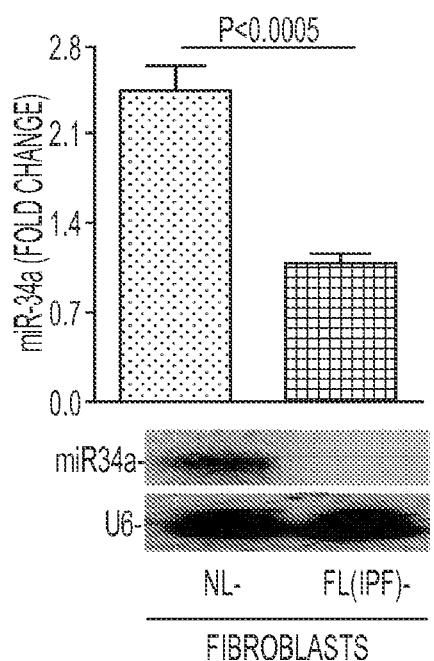

Decreased Caveolin-1, p53 and PAI and Increased uPA in Human FL Fibroblasts from IPF Lungs Cell lysates from NL- and FL-fibroblasts were immunoblotted to reveal changes in the proteins and a miRNA. See FIG. 3A-3B. Basal miR-34a expression was significantly lower in FL-fibroblasts indicating that reduced p53 expression and consequent changes in p53-uPA fibrinolytic system cross-talk contributed to fibrogenesis. Such changes are associated with increased col-I and inhibition of miR-34a. The results further showed that increases in p53-induced miR-34a transcription or stabilization of p53 in human FL-fibroblasts mediated by miR-34a can mitigate lung fibrosis.

Example III

Figure 4A:
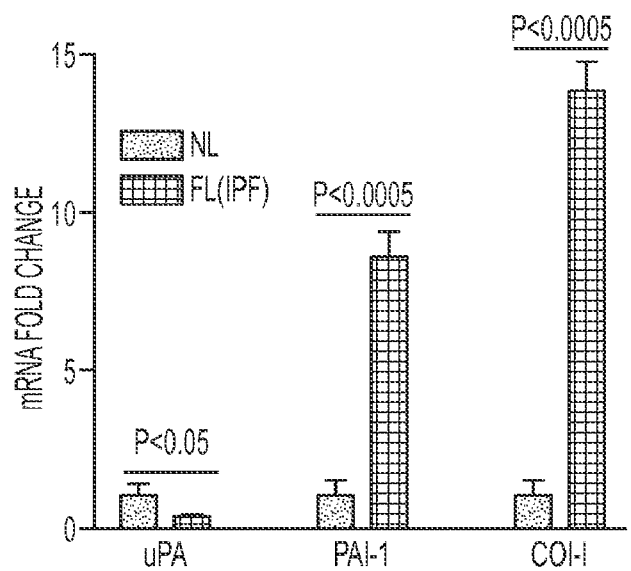
FIGS. 4A-4B. Disparate expression of uPA, uPAR and PAI-1 mRNAs by fibroblasts from IPF and "normal" lungs. Total RNA isolated from lung tissues from "normal" subjects and patients with IPF (FIG. 4A) or from NL-(n=6) and FL-fibroblasts (n=8) (FIG. 4B) were tested for uPA, PAI-1 and col-I mRNA by quantitative real time PCR ((RT-PCR) and normalized to the corresponding levels of β-actin mRNA.
Figure 4B:
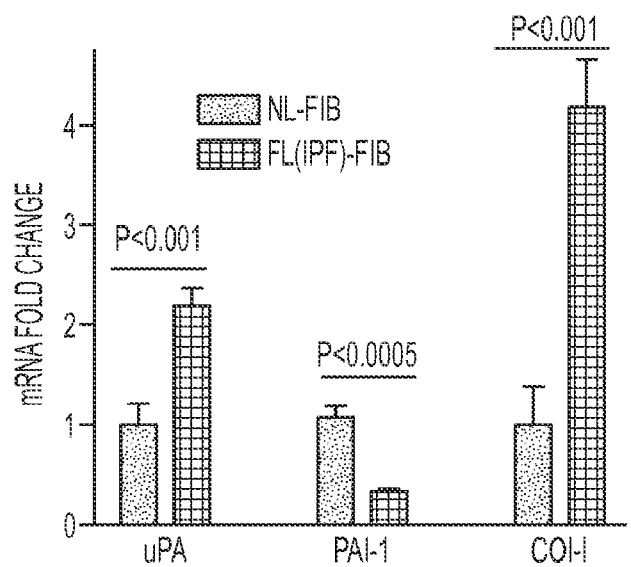

Disparate Expression of uPA, PAI-1 and Col-I mRNAs by Fibroblasts from IPF and "Normal" Lungs Total RNA isolated from lung tissues from "normal" subjects and patients with IPF or from NL—were tested for uPA, PAI-1 and col-I mRNA by quantitative RT-PCR and normalized to the corresponding levels of β-actin mRNA. Results are shown in FIGS. 4A-4B.

Expression of col-I and PAI-1 mRNA significantly increased in IPF lung tissues whereas uPA mRNA was is reduced. Interestingly, unlike IPF lung tissues, col-I and uPA mRNA and lower level of PAI-1 mRNA expression were found in FL-fibroblasts compared to NL-fibroblasts, uPAR protein and mRNA are also elevated in FL-fibroblasts. The elevated PAI-1 in the lung tissues is attributable to increased expression of PAI-1 by lung epithelial cells or macrophages rather than FL(IPF)-fibroblasts. This is consistent with increased expression of col-I, uPA and uPAR, and reduced PAI-1 proteins in FL-fibroblasts from IPF lungs (see FIG. 3A).

Example IV

Differential Expression of uPA and PAI-1 by FL-Vs. NL-Fibroblasts from Mice

FL-fibroblasts were isolated from the lungs of mice 21 days after BLM injury or NL-fibroblasts from control mice exposed to intranasal saline as described elsewhere[26]. The lysates from NL- and FL-fibroblasts were immunoblotted. Changes in the expression of p53, uPA, PAI-1 and col-1 proteins were detected by immunoblotting of cell lysates of NL- ad FL-fibroblasts. (FIG. 5A-5D). Total RNA was extracted from mouse lung tissues NL- and FL-fibroblasts from the lung tissues of mice with BLM-induced fibrosis or control (saline-treated) and tested for uPA, PAI-1 and Col-I mRNA. Proliferative rates of NL- and FL-fibroblasts from mice were compared. Consistent with FL (IPF)-fibroblasts from IPF lungs[2], the baseline rate of proliferation of murine FL(BLM)-fibroblasts were significantly higher than that of NL-fibroblasts (from saline-treated mice), p53 inhibited uPA gene transcription, concurrently bound the PAI-1 promoter and augmented PAI-1 mRNA transcription[33*34]. p53 also inhibited expression of uPA and uPAR via destabilization of their transcripts while stabilizing the PAI-1 transcript[23*25'] Lastly, inhibition of either uPA or uPAR augments p53 expression and downstream p53-mediated induction of PAI-1, thereby increasing cellular senescence and apoptosis. It was concluded that p53-mediated regulation of uPA-fibrinolytic system at the transcriptional and posttranscriptional levels is compromised in FL-fibroblasts due to lack of p53 expression. This leads to increased uPA and uPAR, and inhibition of PAI-1 in these cells.

Example V

CSP Augments p53 Expression Via Induction of miR-34a in FL(IPF)-Fibroblasts

NL- and FL-fibroblasts were treated with PBS, CSP or CP and RNA analyzed for miR-34a by real-time PCR. Also, FL-fibroblasts were cultured in the presence of PBS or CSP or CP with or without miR-34a antisense (miR-34a-AS) or pre-miR-34a (o control miRNA. Conditioned medium (CM) from these cultures was immunoblotted for PAI-1 and cell lysates (CL) were immunoblotted for p53. In one experiment. FL-fibroblasts were treated with PBS or CSP or CP in the presence or absence of miR-34a-AS, pre-miR-34a or control miR. RNA was analyzed for changes in miR-34a by real-time PCR. Results appear in FIGS. 6A-6C.

A series of overlapping deletions were made in CSP and these peptide fragments were tested on FL-fibroblasts for changes in p53, uPA, PAI-1 and col-I (FIG. 6D).

CSP significantly increased miR-34a and p53 expression in FL-but not in NL-fibroblasts. p53 induction by CSP was mimicked by expression of pre-miR-34a alone and abolished by inhibition of miR-34a by miR-34a-AS This indicated that induction of p53 occurs through miR-34a-mediated stabilization.

Figure 11B:
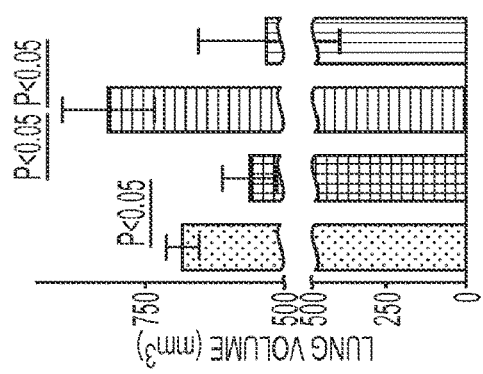
FIGS. 11A-11D. CSP-4 inhibits established lung fibrosis and improves lung function. Mice were exposed to BLM to induce pulmonary fibrosis After 14 d, the mice were injected IV with either vehicle or 1.5 mg/kg body weight of CSP-4 or control peptide ("CP") of scrambled sequence. On d 21 after BLM injury, mice underwent CT scanning examine CSP-4 inhibition of established lung fibrosis (FIG. 11A). One representative example is shown (n=9).
Figure 11D:
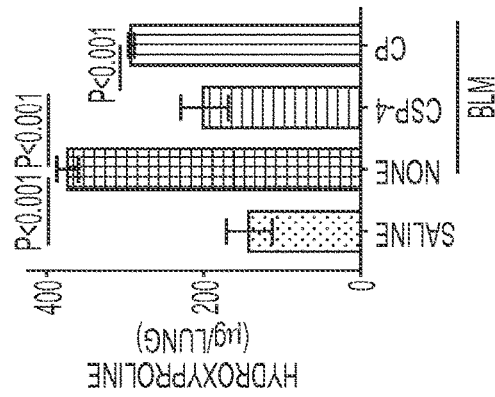
Figure 11A:
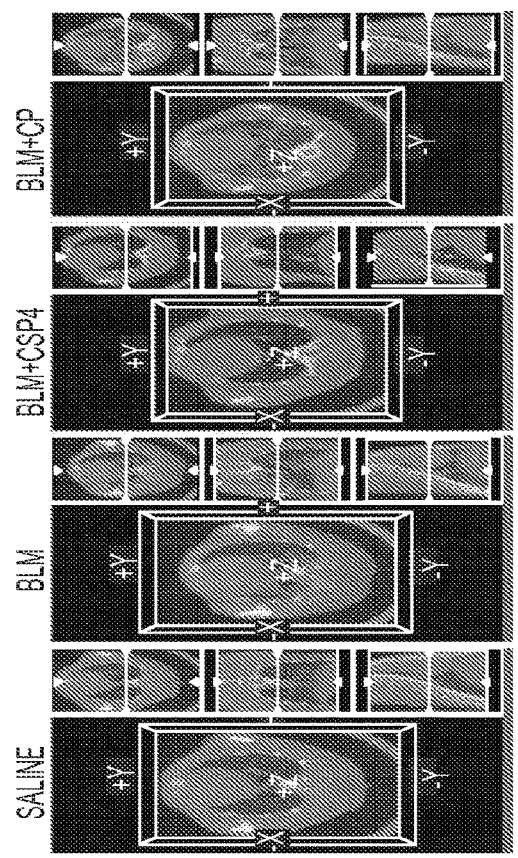
Figure 11C:
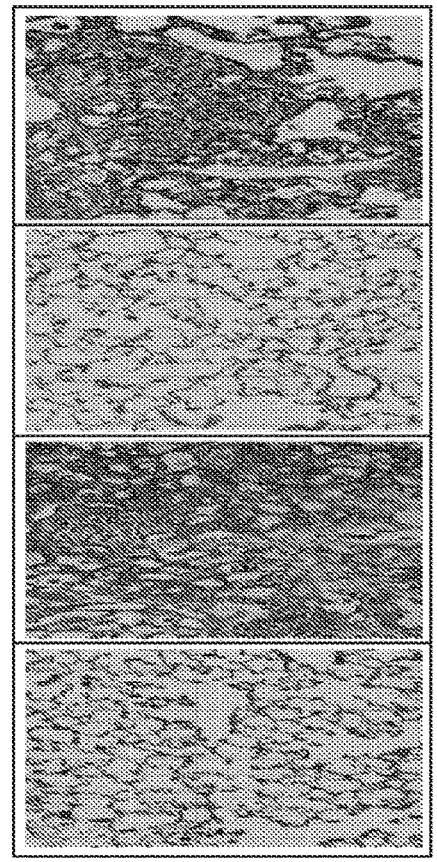

Deletional analysis of the CSP 20mer revealed that an internal 7 amino acid fragment, named CSP-4 and having the sequence FTTFTVT (SEQ ID NO: 1) had the activity of the full length peptide. This supports the conclusion that the salutary effect of CSP-4 in FL-fibroblasts or mice with established lung fibrosis (see FIG. 11A-1 ID), involves control of p53 and miR-34a expression.

Example VI

Mdm2 Mediated Increased Degradation of p53 Proteins in FL (IPF)-Fibroblasts

Figure 7A:
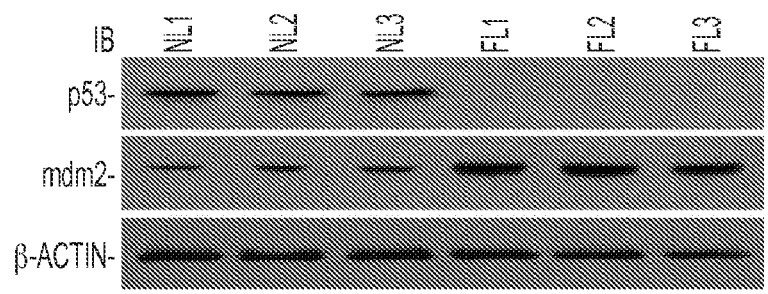
FIGS. 7A-7B. Increased mdm2-mediated degradation of p53 proteins in FL (IPF)-fibroblasts.
Figure 7B:
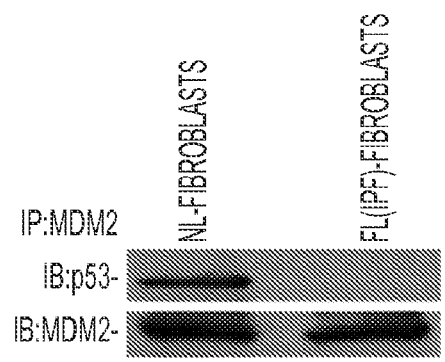

Lysates from NL- and FL-fibroblasts were either immunoblotted for p53, and mdm2 or immunoprecipitated with anti-mdm2 antibody and immunoblotted (IB) for the associated p53 protein. The results showed robust mdm2-p53 interaction in NL-fibroblasts which were absent in FL-fibroblasts (see FIG. 7A-7B) despite elevated levels of mdm2 in the FL-fibroblasts Thus, increased mdm2-mediated degradation of p53 protein contributed to marked suppression of baseline p53 levels in FL-fibroblasts, supporting the use of the therapeutic interventions disclosed herein to target the interaction of mdm2 and p53.

Example VII

Figure 8A:
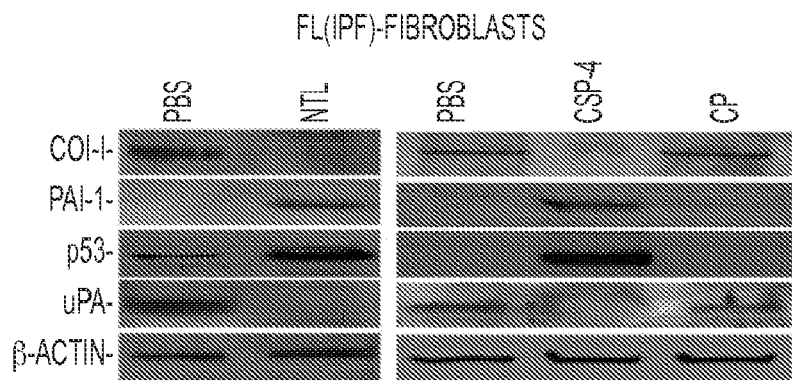
FIGS. 8A-8C. Role of p53-fibrinolytic system cross-talk in nutlin-3a (NTL) or CSP-4-mediated inhibition of col-I expression in FL(IPF)-fibroblasts.
Figure 8B:
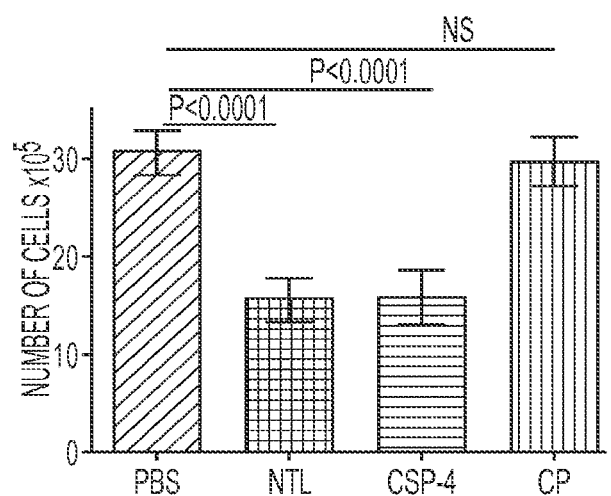

Nutlin-3a-(NTL) or CSP-4-Mediated Inhibition of col-I Expression in FL(IPF)-Fibroblasts; Role of p53-Fibrinolytic System Cross-Talk FL-fibroblasts were exposed to PBS (control), nutlin-3a (10 μM), CSP-4 (10 nM) or CP for 48 hrs. Lysates were immunoblotted for the expression of Col-I, PAI-1, p53, and uPA. Results are shown in FIG. 8A-8B. Cultured FL-were exposed to vehicle (PBS) or nutlin-3a, CSP-4 or CP and counted to assess proliferation. The results showed that both nutlin-3a and CSP-4 inhibited col-I expression and proliferation of FL-fibroblasts. The process involves induction of p53 and PAI-1 expression, and concurrent inhibition of uPA.

Figure 8C:
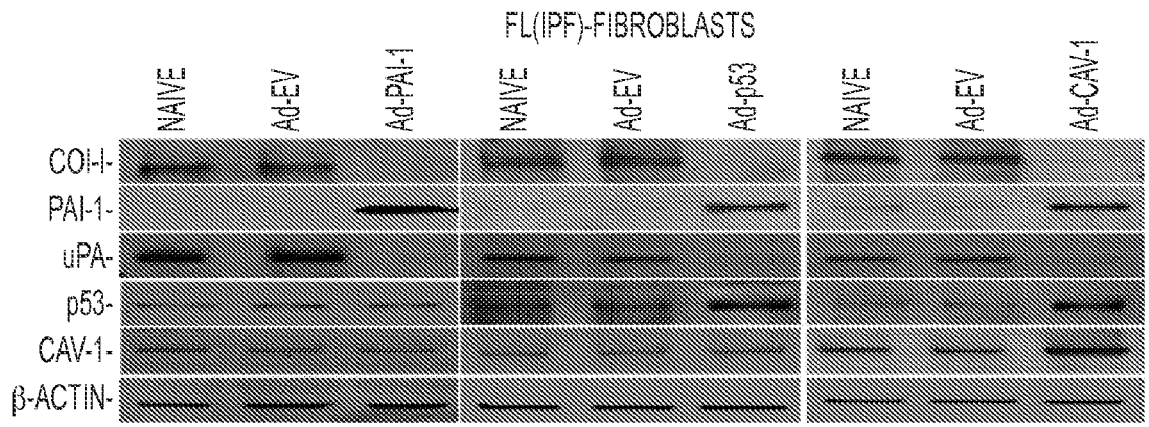

In another experiment (results in FIG. 8C), FL-fibroblasts were transduced with adenovirus vector expressing p53, PAI-1 or caveolin-1 or appropriate vector controls and cultured for 2 days at which time cell lysates were immunoblotted for Col-I, p53, PAI-1, and uPA. Transduction of FL-fibroblasts from IPF lungs with Ad-Cav-1 induced p53 and PAI-1 while inhibiting uPA and col-I expression. The effects of nutlin-3a or CSP-4 on FL-fibroblasts were mimicked by expressing either p53 or PAI-1 or caveolin-1 alone. Therefore, p53-mediated induction of PAI-1 and inhibition of uPA expression contribute to the inhibition of col-I.

Interestingly, treatment of FL-fibroblasts from the lungs of IPF patients or BLM-treated mice with recombinant PAI-1 protein failed to induce apoptosis or senescence (not shown) whereas elevated exogenous PAI-1 induced ATII cell apoptosis both in vitro and in vivo. The resistance of FL-fibroblasts to exogenous PAI-1 would enable these cells to flourish in the PAI-1 protein-rich environments of IPF or BLM-injured lungs.

Example VIII

Figure 9A:
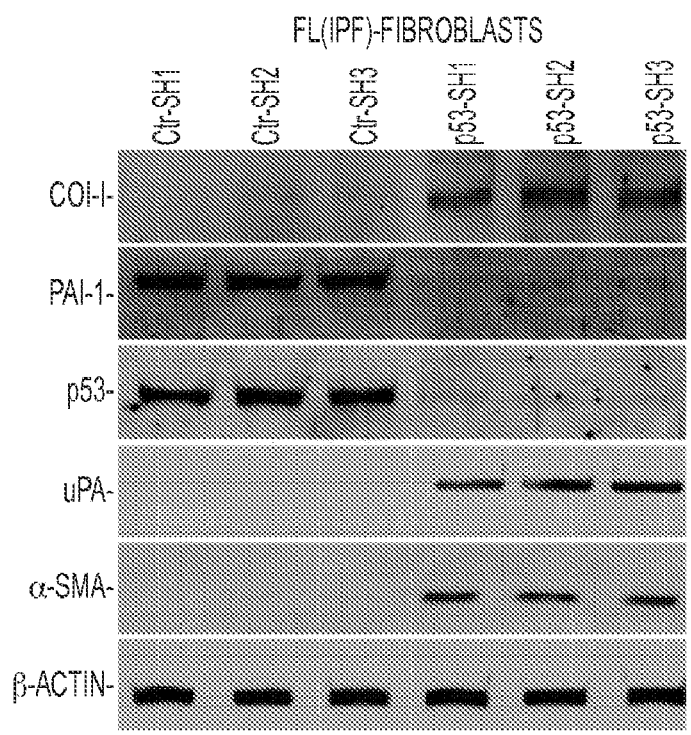
FIGS. 9A-9B. Role of p53-fibrinolytic system cross-talk in induction of col-I expression in NL-fibroblasts. NL-fibroblasts isolated from histologically "normal" human lungs were treated with p53 shRNA in lentiviral vector to inhibit baseline p53 expression. Control cells were treated with non-specific (Ctr) shRNA.
Figure 9B:
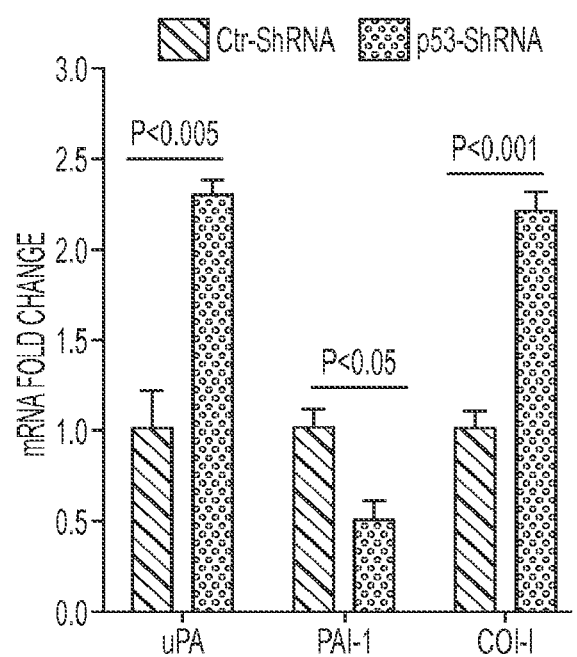

Role of p53-Fibrinolytic System Cross-Talk in Induction of Col-I Expression in NL-Fibroblasts NL-fibroblasts isolated from histologically "normal" human lungs[2] (S. Shetty et al. 1996, supra) were transfected with a lentiviral vector carrying p53 shRA to inhibit baseline p53 expression. Control cells were similarly treated with a non-specific shRNA. Conditioned medium from the cultures was immunoblotted for PAI-1, uPA, and soluble col-I, and cell lysates were tested for p53 and a-SMA. Total RNA isolated from these fibroblasts were analyzed for changes in the expression of uPA, PAI-1 and col-I mRNA by quantitative RT-PCR. The results (in FIG. 9A-9B) show that inhibition of p53 expression in NL-fibroblasts augmented uPA, col-I and a-SMA but inhibited PAI-1. This supports the link described here between p53-mediated changes in the uPA system and fibrogenesis.

Example IX

Nutlin-3a Inhibits Lung Fibrosis in BLM-Treated Mice

Figure 10A:
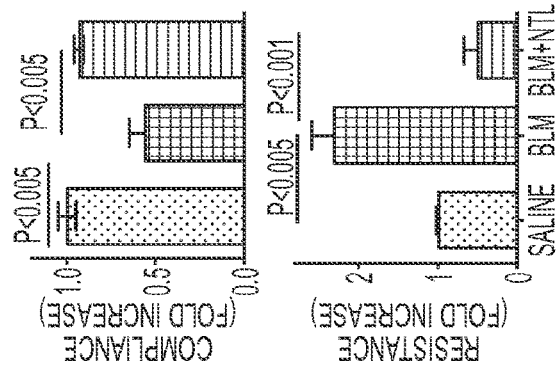
(FIG. 10C) Lung sections were subjected to trichrome staining to assess lung architecture and collagen deposition as an indication of lung fibrosis.
(FIG. 10D) Whole lung homogenates were analyzed for total collagen (hydroxyproline) and desmosine content as an independent assessment of changes in ECM.
Figure 10B:
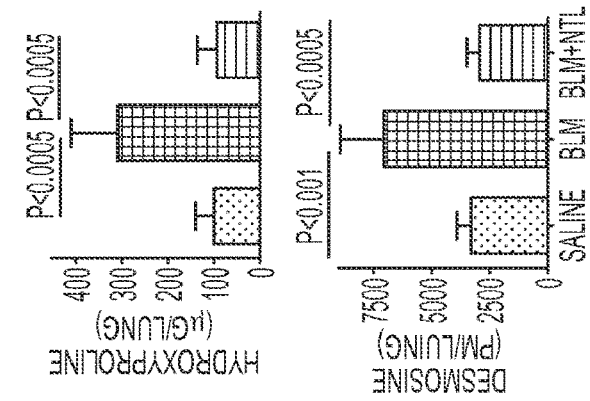
Figure 10C:
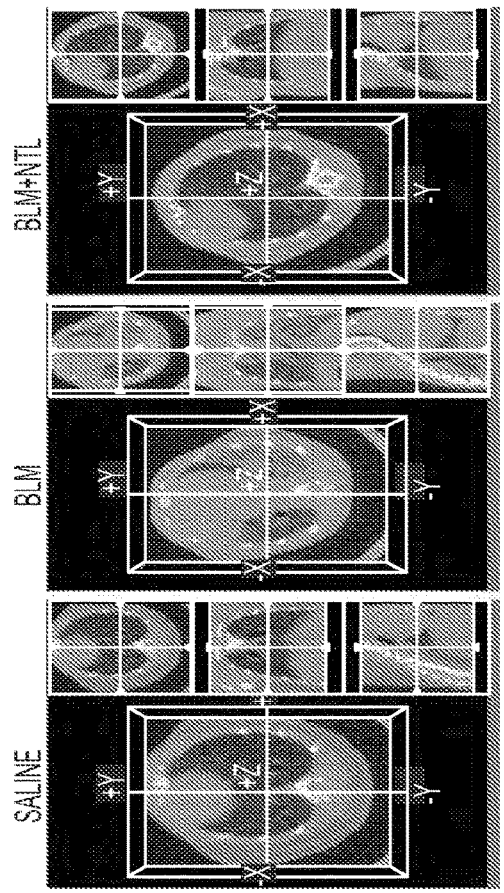
Figure 10D:
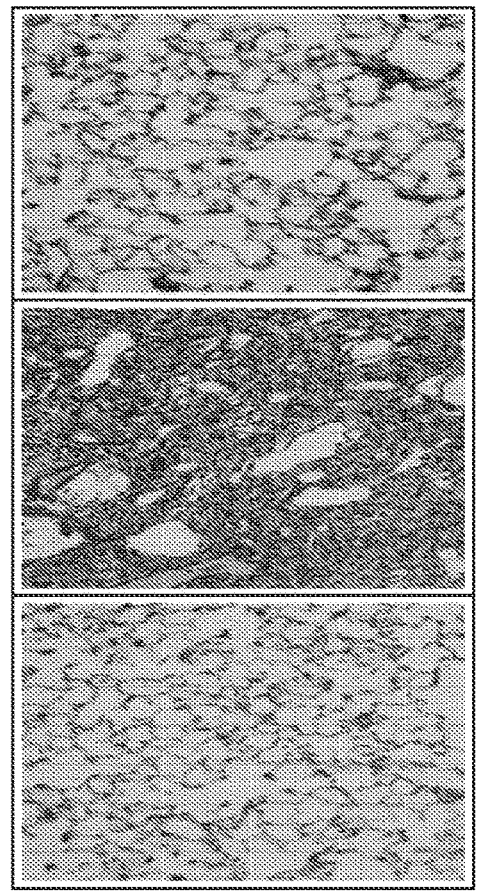

Mice exposed to BLM (or saline in controls) for 14 d to induce lung fibrosis were injected IV with nutlin-3a (10 mg/kg body weight) (Zhang et al. supra) or a vehicle control to determine and the effect on established lung fibrosis was examined. Fibrosis was evaluated by CT scanning and lung function (compliance and resistance) were measured using the Flexivent system. Lung sections were subjected to trichrome staining and H & E staining (the latter not shown) to assess lung architecture and collagen deposition as an indication of fibrosis. Finally, whole lung homogenates were analyzed for total collagen (hydroxyproline) and desmosine content (Bhandary Y P et al, Am J Physiol: Lung Cell Mol Physiol 302:1.463-73, 2012, Bhandary Y P et al, Am J Pathol, 183: 131-43 2013) as an independent assessment of the ECM. Results (FIGS. 10-10D) of all the above tests indicated a beneficial effect of nutlin-3a on lung fibrosis. Oral administration of Nutlin-3a 14 days after BLM injury likewise inhibited pulmonary fibrosis in mice.

Example X

CSP-4 Peptide Inhibits Established Lung Fibrosis and Improves Lung Function

Mice were exposed to BLM to induce pulmonary fibrosis. After 14 d, the mice were injected IV with either vehicle or 1.5 mg/kg body weight of CSP-4 (SEQ ID NO: 1) or control peptide (scrambled sequence of same amino acids; CP, SEQ ID NO:5)) at 1.5 mg/kg body weight or vehicle was injected IV into mice exposed to BLM 14 days earlier. One week later, mice were tested by CT scanning to evaluate lung fibrosis. Lung volume was measured in the same mice using quantitative CT renditions. Lung sections were subjected stained (trichrome and H&E to assess collagen deposition as an indicator of lung fibrosis. Whole lung homogenates were analyzed for total hydroxyproline and desmosine content (the latter results not shown). Results are in FIGS. 11A-1 ID. All tests showed that CSP-4 inhibited BLM-induced lung fibrosis. Consistent with the in vitro effects of both CSP and CSP-4 on FL-fibroblasts from IPF lungs (See FIG. 6D), CSP-4 exerted a beneficial effect in vivo against established lung fibrosis, mimicking the salutary effects of the full length peptide, CSP (SEQ ID NO:3).

Example XI

CSP-4 Peptide and Nutlin-3a Inhibit Proliferation of FL-Fibroblasts

Figure 12A:
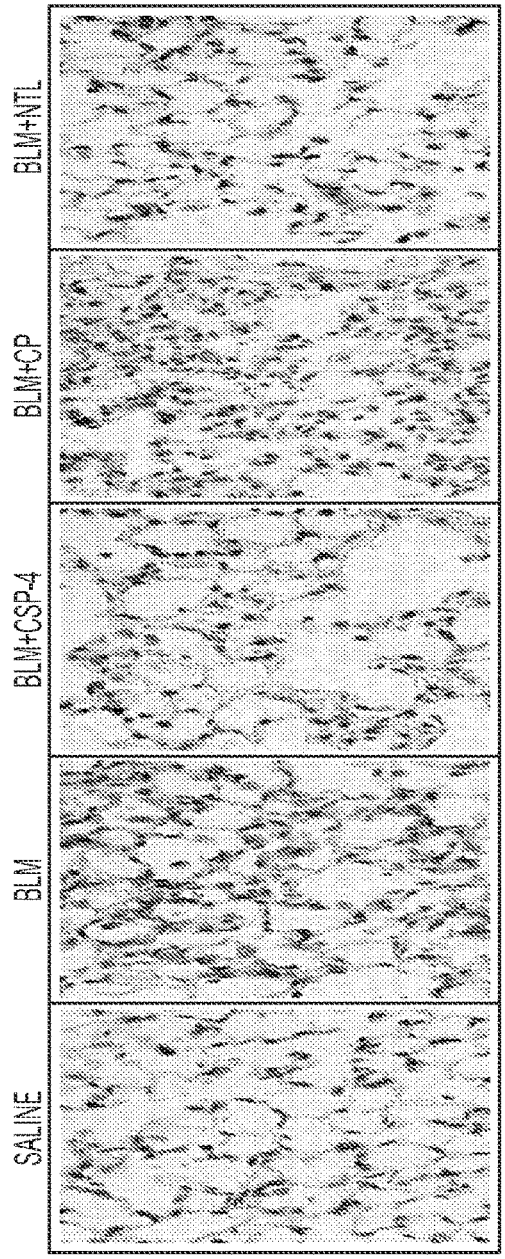
FIGS. 12A-12C. CSP-4 or nutlin-3a (NTL) inhibits proliferation of FL-fibroblasts. Mice were exposed to BLM for 14 d to induce significant lung fibrosis or to saline (fibrosis controls). 14 d later, mice exposed to BLM were treated with CSP-4 or CP, or nutlin-3a (see FIGS. 1OAOD/1 1A-D).
Figure 12C:
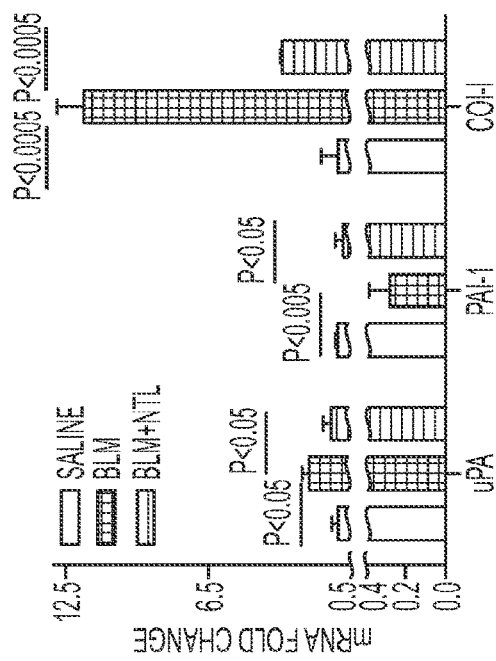
Figure 12B:
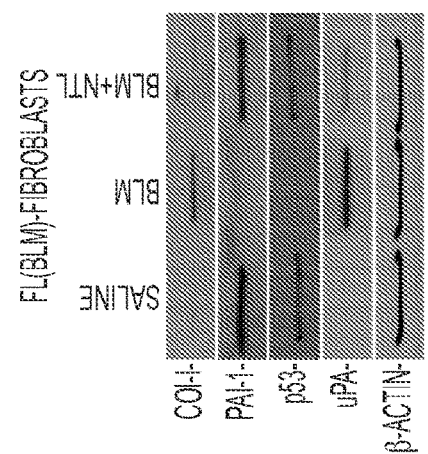

Mice exposed to BLM 14 days earlier were treated with CSP-4 or its control (CP) or Nutlin-3a IV (as in Examples IX and X). Seven days later lung sections were obtained and subjected to IHC for Ki-67 to assess cell proliferation (see FIG. 12A). The increased staining for ki-67 antigens observed in lung sections of fibrotic mice was significantly reduced by treatment with nutlin-3a or CSP-4. Fibroblasts isolated from the lungs of these animals (as described in Example X) were tested for the changes in expression of col-I, p53 and downstream uPA and PAI-1 proteins by Western blotting, and mRNA by quantitative RT-PCR (see FIGS. 12B-12C). FL-fibroblasts from mice with established BLM-induced fibrosis showed increased uPA and col-I mRNA and protein expression compared to NL-fibroblasts from mice without lung injury. These cells also showed minimal p53 and PAI-1 expression. However, in fibroblasts from mice treated with nutlin-3a, uPA and col-I protein and mRNA expression were significant suppressed. These changes were associated with marked induction p53 protein, and PAI-1 protein and mRNA expression, indicating that restoration of p53-fibrinolytic system cross-talk mitigates fibrosis.

Example XII

Inhibition of Fibrotic Changes by Treatment Ex Vivo with CSP-4 or Nutlin-3a

Mice were exposed to intranasal BLM for 21 d to induce pulmonary fibrosis, sacrificed, and their lungs excised and chopped into small pieces and placed into culture medium. These tissue samples were thereafter treated with 10 nM CSP-4 peptide, control peptide (CP) or nutlin-3a for 72 h. Conditioned medium and tissue lysates were and analyzed for changes in col-I and α-SMA by Western blotting. The results (FIG. 13) showed that treatment of fibrotic lung tissue explants with CSP-4 or nutlin-3a inhibited fibrosis ex vivo. The full length CSP peptide yielded similar inhibition of col-I and a-SMA (results not shown). Nutlin-3a and CSP-4 are expected to act similarly to affect human IPF lung tissues ex vivo. The present inventors' results provided herein and in recent reports (e.g., Bhandary et al, 2012, 2013, supra), strongly support the conception that p53-mediated downstream changes in uPA and PAI-1 regulates viability of FL-fibroblasts.

Example XIII p53 Expression in FL-Fibroblasts and Downstream Reversal of the uPA-Fibrinolytic System Mitigates Pulmonary Fibrosis In Vivo The results reported herein and elsewhere (Bhandary Y P et al. 2012, supra) Shetty S K et al αI., Aτη J Respir Cell Mol Biol 47:474-83, 2012) show that IP or IV administration of CSP or CSP-4 (FIG. 11A-1 ID), or IV or oral administration of nutlin-3a in wild type (WT) mice (FIG. 10A-10D) beginning 14 d after BLM mitigates established lung fibrosis. Therefore, mdm2-mediated degradation of p53 protein and loss of downstream p53-uPA system cross-talk increases FL-fibroblast viability and production of ECM in vivo, leading to destruction of lung architecture and loss of lung function Because patients often present with advanced stages of IPF (at the time of initial diagnosis), the mechanisms by which nutlin-3a and CSP-4 inhibit established lung fibrosis are evaluated and the downstream targets of nutlin-3a and CSP-4 are identified. These studies utilize lung tissues from IPF patients and mice with advanced lung fibrosis due to BLM lung injury. The contribution and the specificity of p53-uPA system crosstalk is confirmed by using uPA-, uPAR-, PAI-1- and p53-deficient mice.

A. Determination of the Effects of Nutlin-3a and CSP-4 Treatment on Fibrosis Using FL (IPF)-Tissues Ex Vivo.

Figure 13:
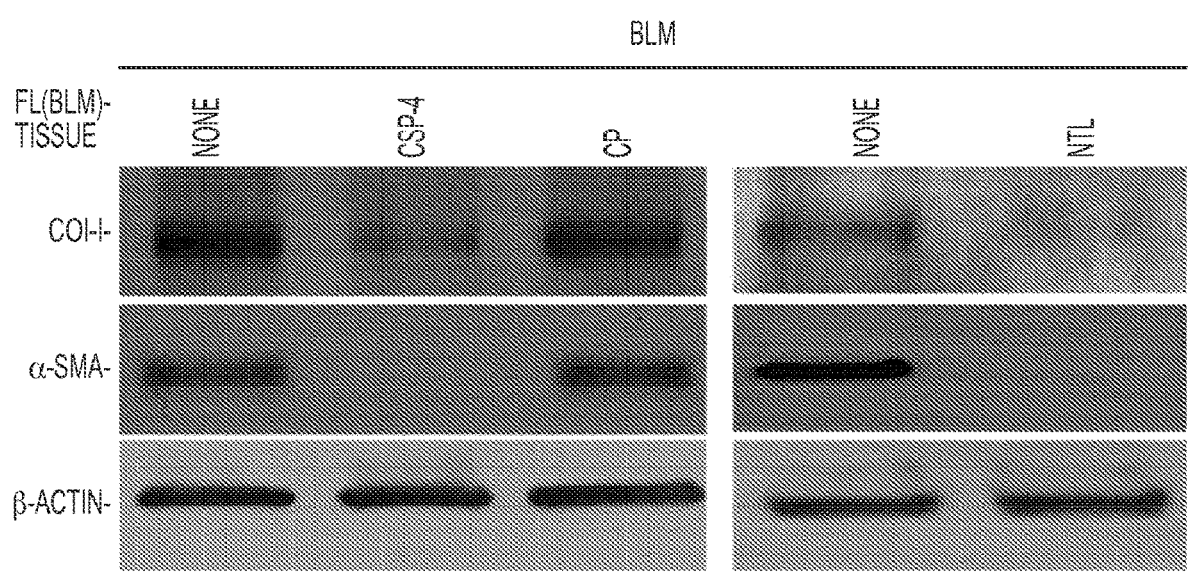
FIG. 13. Inhibition of BLM-induced pulmonary fibrosis by ex vivo treatment of WT mice lung tissues with CSP-4 or nutlin-3a (NTL). Mice were exposed to intranasal BLM for 21 d to induce pulmonary fibrosis. These mice (n=3) were sacrificed, lungs were excised, chopped into small pieces and placed in culture dishes with DMEM medium containing 10% fetal bovine serum. The tissue samples were later treated with CSP-4 (10 nM), control peptide (CP) and nutlin-3a (TL) (10 μM) for 72 h. Conditioned medium and tissue lysates were prepared and analyzed for changes in col-I, a-SMA and β-actin by Western blotting.

Freshly dissected FL-lung tissues from IPF patients are treated with nutlin-3a (10 µM) or CSP-4 (10 nM) for 3 to 7 days (see FIG. 13). Lung tissues are homogenized and tested for changes in ECM (hydroxyproline and desmosine). Controls include fibrotic lung (FL)-tissues from IPF patients treated with vehicle or control peptide, CP or naive lung tissues maintained in culture medium. Other controls include NL-tissues resected from histologically "normal" lungs. De-identified patient ("normal" and IPF) lungs that were not suitable for transplantation and donated for medical research are obtained through HAM (Edison, N.J.) and the NDRI (Philadelphia. Pa.) and used for ex vivo studies. Fibroblasts are isolated from these tissues and analyzed for changes in p53, uPA, uPAR and PAI-1 expression, production of ECM and viability. Changes in rate of ECM synthesis are also measured FL-tissue explants from patients with IPF have elevated synthesis of ECM when compared to expression levels in the slices of NL-tissues from control subjects. However, FL-lung explants treated with either nutlin-3a or CSP-4 show significantly reduced ECM synthetic rates when compared to those remain untreated or exposed to either vehicle alone or CP. Fibroblasts isolated from the IPF explants treated with either nutlin-3a or CSP-4 show elevated levels of p53, miR-34a and PAI-1, and reduced uPA and uPAR expression. Phosphorylation of Akt and expression of PDGFR-β mRNA and protein also are reduced in fibroblasts from IPF explants treated with nutlin-3a or CSP-4. The rate of proliferation and production of ECM of these fibroblasts are significantly lower than FL-fibroblasts from untreated or vehicle- or CP-treated controls but comparable to that of fibroblasts isolated from NL-tissues.

B. Role of p53 and miR-34a in the Control of Lung Fibrosis.

Based on the above results, it is predicted that lack of p53 and miR-34a expression by FL-fibroblasts contributes to lung fibrosis and that restoration of baseline p53 expression by nutlin-3a or CSP-4 via induction of miR-34a mitigates lung fibrosis. Since maximum lung fibrosis occurs between 14-28 days after BLM injury (Bhandary Y P et ah, 2012, supra; Bhandary Y P et ah, 2013, supra; and data presented here) pre-miR-34a is expressed in mouse lung fibroblasts by IV injection of lentivirus (LV) containing proa2(I) collagen promoter with pre-miR-34a at 14 and 21 days after BLM lung injury. Lung fibrosis is evaluated 28 days later. The role of miR-34a in nutlin-3a- or CSP-4-mediated mitigation of lung fibrosis is confirmed by LV expression of miR-34a-AS in fibroblasts using proa2(I) promoter in fibrotic lungs.

The role of p53 in the salutary effects against lung fibrosis is confirmed directly by expressing p53 in lung fibroblasts of mice with established fibrosis using LV or Ad-p53 containing proa(I) collagen promoter with or without inhibition of miR-34a. Lung fibrosis and miR-34a expression is evaluated, e.g., 28 days after BLM injury. Alternatively or additionally, p53 expression is inhibited using LV shRNA in WT mice with BLM-induced lung fibrosis or use p53-deficient mice with established lung fibrosis (Davis D W et ah, J Exp Med 792:857-869, 2000). These mice are then exposed to nutlin-3a or CSP-4, e.g., 14 and 21 d after BLM injury. Control mice with lung fibrosis are exposed to non-specific shRNA or na'fve WT mice and treated with nutlin-3a or CSP-4. The mice are tested for lung fibrosis and miR-34a expression, e.g., 28 d after initiation of BLM injury. The contribution of the p53-uPA system cross-talk is confirmed by exposing WT, p53-, uPA-, uPAR- and PAI-1-deficient mice to BLM for 14-21 d to induce lung fibrosis, alter miR-34a expression in fibroblasts as described above, and testing the effects on fibrosis, e.g., on day 28 after BLM injury.

C. Restoration of p53 Expression and Downstream p53-uPA Fibrinolytic System Cross-Talk by Nutlin-3a or CSP-4 Inhibits Lung Fibrosis.

The contribution of p53-uPA fibrinolytic system cross-talk in mitigation of lung fibrosis by nutlin-3a and CSP-4 in mice is confirmed by isolating fibroblasts from these mice, e.g., 28 d after BLM injury. These cells are tested for changes in p53, uPA, uPAR and PAI-1 expression and production of ECM. we expect to find that FL-fibroblasts isolated from the lungs of mice with BLM injury will show elevated uPA and uPAR, viability and production of ECM. These FL-fibroblasts show minimal p53 and PAI-1 expression compared to NL-fibroblasts from uninjured lungs. I-However, fibroblasts from the lungs of mice with BLM-induced fibrosis exposed to nutlin-3a or CSP-4 show elevated p53. These cells are less proliferative with minimal ECM production. uPA and uPAR expression are reduced while PAI-1 increases compared to FL-fibroblasts obtained from BLM injured mice. uPA, uPAR and PAI-1 levels in the lung fibroblasts of BLM+nutlin-3a or BLM+CSP-4 treated mice are comparable to NL-fibroblasts isolated from uninjured mice.

To confirm the involvement of p53-uPA system cross-talk, FL-fibroblasts extracted from BLM injured mouse lungs are transduced with Ad-p53. The fibroblasts from BLM injured lungs exposed to nutlin-3a or CSP-4 are positive controls while those exposed to CP or Ad-EV are negative controls. The cells are tested for changes in uPA, uPAR and PAI-1.

Transduction of Ad-p53 or treatment with nutlin-3a or CSP-4 augments PAI-1 and inhibits uPA and uPAR expression. These cells suppress production of ECM and a rate of proliferation compared to FL-fibroblasts exposed to CP or Ad-EV. FL-fibroblasts from BLM mice express remarkably low levels of caveolin-1 and expression of caveolin-1 mitigates excess production of ECM. Therefore, FL-fibroblasts are transduced with Ad-Cav-1 to see whether p53 and p53-mediated downstream changes in uPA fibrinolytic system, ECM and cellular viability are reduced compared to those treated with Ad-EV.

D. Role of Nutlin-3a- or CSP-4-Mediated in Inhibition of Akt Phosphorylation in Mitigation of Lung Fibrosis.

FL-fibroblasts display elevated phosphorylation of Akt and expression of PDGFR-β which provides survival signals (Stambolic V et al Mol Cell 8:317-25, 2001; Li J et al. J Environ Pathol Toxicol Oncol 23:253-66, 2004; Hoyle G W et al. Am J Pathol 154: 1163-15, 1999, Meinecke A K et al. Blood 14: \\9:5931-42, 2012) Further, p53 augments expression of PTEN (Stambolic et al. supra; Mayo L D, et al J Biol Chem 277:5484-89, 2002) and inhibits PDGFR-β (Widau R C et al, Mol Cell Biol 32:4270-82, 2012; Thornton J D et al, Cell Cycle 4:316-9, 2005) whereas PAI-1 inhibits Akt phosphorylation (Shetty S K et al, 2012, supra; Stambolic et al, supra, Malinowsky K et al. Transl Oncol 5:98-104, 2012). Transduction of FL-fibroblasts with Ad-Cav-1 inhibits phosphorylation of Akt through increased PTEN activity (Tourkina E et al Open Rheumatol J. 6: 116-22, 2012; Wang X M et al J Exp Med 203:2895-906, 2006, Xia H et al Am J Pathol 176.2626-37, 2010).

Results provided herein showed that nutlin-3a and CSP-4 augment p53 and repress production of ECM in FL-fibroblasts, and mitigate BLM-induced lung fibrosis. The present inventors therefore conceived that inhibition of Akt and PDGFR-β survival signals in FL-fibroblasts, due to induction of p53 and changes in p53-uPA fibrinolytic system cross-talk, mitigates fibrosis. To test this. FL-fibroblasts from BLM injured mouse lungs are tested for phosphorylation of Akt and expression of PDGFR-β The responses are compared with fibroblasts extracted from mice treated with nutlin-3a or CSP-4 or CP after BLM injury. FL-fibroblasts from BLM injured mice are expected to have minimum baseline p53 expression and elevated phosphorylation of Akt. PDGFR-β expression is expected to increase in FL-fibroblasts. p53 should be augmented in fibroblasts from mice treated with either nutlin-3a or CSP-4, leading to inhibition of Akt phosphorylation and PDGFR-β expression. Since FL-fibroblasts from BLM injured mice express more uPA and uPAR, these fibroblasts will manifest increased viability and ECM compared to fibroblasts from mice treated with BLM plus nutlin-3a or CSP-4. However, transduction of FL-fibroblasts from BLM mice with Ad-p53 or Ad-Cav-1 will reduce phosphorylation of Akt and PTEN, PDGFR-β expression, cell viability and production of ECM compared to Ad-EV treated control cells. Inhibition of p53 using shRNA will inhibit ECM production, PDGFR-β expression and viability of FL-fibroblasts exposed to Ad-Cav-1 or nutlin-3a or CSP-4. These cells will show elevated uPA and uPAR with minimal PAI-1 compared to FL-fibroblasts transduced with Ad-Cav-1 or nutlin-3a or CSP-4 in the presence of control shRNA.

According to the present invention, because IPF patients often present with advanced fibrotic disease at the time of diagnosis, targeting of FL-fibroblasts has a clinical advantage over prevention of ATII cell apoptosis or epithelial mesenchymal transition. Nutlin-3a and CSP-4 effectively induce p53 only in FL-fibroblasts for markedly reduced baseline p53 and elevated mdm2 expression in FL-fibroblasts compared to NL-fibroblasts or ATII cells in injured lungs. This is particularly true with ATII cell caveolin-1 and p53 expression, which is markedly increased in the lungs of patients with IPF or mice with BLM lung injury. Based on this experience, further induction of p53 in ATII cells is not anticipated in response to nutlin-3a or CSP-4 because of elevated baseline levels in BLM or IPF lungs. Indeed, the present inventors and colleagues found that CSP or CSP-4 inhibited BLM- or cigarette smoke-induced ATII cell p53 expression and apoptosis (Bhandary et al, 2012, 2013, supra; Shetty S K et al, Am J Respir Cell Mol Biol 47:474-83, 2012) by blocking ATM kinase-mediated serine-15 phosphorylation of p53 by competing with caveolin-1, which is otherwise induced in ATII cells due to BLM injury for protein phosphatase 2A-C (Volonte D et al., J Biol Chem 284:5462-66, 2009). In addition, nutlin-3a action on neutrophils and macrophages could have a beneficial effect against inflammation via p53-mediated inhibition of NF-κB DNA binding activity and production of proinflammatory cytokines (Liu G et al., J Immunol 182:5063-71, 2009).

Therefore, the benefits of nutlin-3a and CSP-4 interventions outweigh any potential deleterious or off-target effects. Excessive proliferation and production of proa(I) collagen by the FL-fibroblasts should lead to efficient expression of pre-miR-34a and miR-34a antisense in FL-fibroblasts using LV after BLM-induced lung fibrosis in mice (Liu X et al., Am J Physiol: Lung Cell Mol Physiol 29&L819-29, 2010; Merkel O et al, Cell Cycle 9:2764-8, 2010).

Transduction of BLM-injured lungs with Ad-cav-1 (Wang X M et al. J Exp Med 203:2895-906, 2006) inhibits fibrosis despite of increased caveolin-1 expression by ATII cells during BLM injury. This suggests that expression of p53, pre-miR-34 and miR-34a antisense still should be effective even if they transduce NL-fibroblasts as well as FL-fibroblasts in mice with established pulmonary fibrosis.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A composition comprising
    a polypeptide having an amino acid sequence of FTTFTVT (SEQ ID NO: 1) with 1 to 5 additional residues at one or both ends of FTTFTVT (SEQ ID NO: 1),
    wherein the polypeptide has an internalization sequence at the N-terminal end or the C-terminal end.

2. The composition of claim 1, wherein the composition further comprises a pharmaceutically acceptable carrier.

3. The composition of claim 1, wherein the internalization sequence is located at the N-terminal end of the polypeptide.

4. The composition of claim 1, wherein an internalization sequence is located at the C-terminal end of the polypeptide.

5. The composition of claim 1, wherein the polypeptide comprises a cap at its N-terminus.

6. The composition of claim 1, wherein the polypeptide comprises a cap at its N-terminus and C-terminus.

7. The composition of claim 5, wherein the cap comprises an acyl or amido group.

8. The composition of claim 1, wherein the polypeptide comprises L-amino acids.

9. The composition of claim 1, wherein the polypeptide comprises at least one D-amino acid.

10. The composition of claim 1, wherein the polypeptide is cyclized.

11. A method of treating a subject having a disease or condition characterized by fibrosis, the method comprising administering an effective amount of a composition of claim 1 to the subject.

12. The method of claim 11, wherein the composition is administered intranasally or intrabronchially to the subject.

13. The method of claim 11, wherein the fibrosis is pulmonary fibrosis.

14. The method of claim 11, wherein the fibrosis is idiopathic pulmonary fibrosis.

15. The method of claim 11, wherein the composition is administered by instillation into the lungs of the subject.

16. The method of claim 11, wherein the composition reduces fibrosis in the subject.

* * * * *

SEQUENCE LISTING

<160> NUMBER OF SEQ ID NOS: 14

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Phe Thr Thr Phe Thr Val Thr
1               5

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide - Scaffolding domain of human caveolin-1

<400> SEQUENCE: 2

Asp Gly Ile Trp Lys Ala Ser Phe Thr Thr Phe Thr Val Thr Lys Tyr
1               5                   10                  15

Trp Phe Tyr Arg
            20

<210> SEQ ID NO 3
<211> LENGTH: 178
<212> TYPE: PRT
<213> ORGANISM: Homo sapiens

<400> SEQUENCE: 3

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Asn Tyr His Tyr Leu Glu Ser Ser Met Thr Ala Leu Tyr Thr Leu Gly
1               5                   10                  15

His

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Trp Gly Ile Asp Lys Ala Phe Phe Thr Thr Ser Thr Val Thr Tyr Lys

```
                1               5                   10                  15

Trp Phe Arg Tyr
            20

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide - - Penetratin derived from
      the third alpha helix of Antennapedia homeodomain

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Arg Gln Ile Lys Ile Phe Phe Gln Asn Arg Arg Met Lys Trp Lys Lys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Gln Ile Lys Ile Trp Phe Gln Asn Arg Arg Met Lys Phe Lys Lys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Arg Gln Ile Lys Ile Phe Phe Gln Asn Arg Arg Met Lys Phe Lys Lys
1               5                   10                  15

<210> SEQ ID NO 10
<211> LENGTH: 27
<212> TYPE: PRT
<213> ORGANISM: Artificial Sequence
<220> FEATURE:
<223> OTHER INFORMATION: Synthetic peptide - Transportan

<400> SEQUENCE: 10

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 11
<211> LENGTH: 21
<212> TYPE: PRT
<213> ORGANISM: Artificial Sequence
```

```
<220> FEATURE:
<223> OTHER INFORMATION: Synthetic peptide

<400> SEQUENCE: 11

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Asp Gly Ile Trp Lys Ala Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Lys Tyr Trp Phe Tyr Arg
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Arg Gln Ile Lys Ile Trp Phe Gln Asn Arg Arg Met Lys Phe Lys Lys
1               5                   10                  15
```